(12) United States Patent
Lu et al.

(10) Patent No.: US 8,222,616 B2
(45) Date of Patent: Jul. 17, 2012

(54) METHOD FOR ADAPTING FRACTIONATION OF A RADIATION THERAPY DOSE

(75) Inventors: Weiguo Lu, Madison, WI (US); Mingli Chen, Madison, WI (US); Quan Chen, Madison, WI (US); Kenneth J. Ruchala, Madison, WI (US); Gustavo H. Olivera, Madison, WI (US)

(73) Assignee: Tomotherapy Incorporated, Madison, WI (US)

( * ) Notice: Subject to any disclaimer, the term of this patent is extended or adjusted under 35 U.S.C. 154(b) by 508 days.

(21) Appl. No.: 12/258,783

(22) Filed: Oct. 27, 2008

(65) Prior Publication Data

US 2009/0110145 A1 Apr. 30, 2009

Related U.S. Application Data

(60) Provisional application No. 60/982,448, filed on Oct. 25, 2007.

(51) Int. Cl.
*G01N 23/00* (2006.01)
*A61N 5/10* (2006.01)
*A61B 9/00* (2006.01)

(52) U.S. Cl. ........... 250/491.1; 250/492.23; 250/390.03; 378/65; 382/128; 600/439

(58) Field of Classification Search ................ 600/427, 600/411, 407, 315, 426, 436, 437, 439, 443; 382/128, 131, 132; 250/491.1, 492.1, 493.1, 250/492.21, 492.22, 492.23, 494.1, 503.1, 250/505.1, 526, 390.03; 378/64, 65, 68, 378/145–161, 165
See application file for complete search history.

(56) References Cited

U.S. PATENT DOCUMENTS

| | | | |
|---|---|---|---|
| 4,149,081 A | 4/1979 | Seppi | |
| 4,455,609 A | 6/1984 | Inamura et al. | |
| 4,998,268 A | 3/1991 | Winter | |
| 5,008,907 A | 4/1991 | Norman et al. | |
| 5,027,818 A | 7/1991 | Bova et al. | |
| 5,044,354 A | 9/1991 | Goldhorn et al. | |
| 5,065,315 A | 11/1991 | Garcia | |
| 5,117,829 A | 6/1992 | Miller et al. | |
| 5,317,616 A | 5/1994 | Swerdloff et al. | |
| 5,332,908 A | 7/1994 | Weidlich | |

(Continued)

FOREIGN PATENT DOCUMENTS

JP 10052421 2/1998

(Continued)

OTHER PUBLICATIONS

Di Yan, On-line Strategy of Daily Dose Prescription in Adaptive Radiotherapy, Proceedings of the 22nd Annual EMBS International Conference, Jul. 23-28, 2000, Chicago, IL, pp. 2145-2148.

(Continued)

*Primary Examiner* — Bernard E Souw
(74) *Attorney, Agent, or Firm* — Michael Best Friedrich LLP

(57) ABSTRACT

A system and method of adapting a radiation therapy treatment plan for a patient by varying the fraction size delivered to the patient on any individual day, based at least partially on the use of daily patient registration (i.e., taking images of the patient before each fraction is delivered to see the position and size of the tumor on that day). The fraction size can be dynamically altered based upon the biology of the tumor.

39 Claims, 16 Drawing Sheets

Day 1

Day 2

U.S. PATENT DOCUMENTS

| Patent | Date | Inventor |
|---|---|---|
| 5,335,255 A | 8/1994 | Seppi et al. |
| 5,351,280 A | 9/1994 | Swerdloff et al. |
| 5,391,139 A | 2/1995 | Edmundson |
| 5,394,452 A | 2/1995 | Swerdloff et al. |
| 5,405,309 A | 4/1995 | Carden, Jr. |
| 5,442,675 A | 8/1995 | Swerdloff et al. |
| 5,446,548 A | 8/1995 | Gerig et al. |
| 5,471,516 A | 11/1995 | Nunan |
| 5,528,650 A | 6/1996 | Swerdloff et al. |
| 5,548,627 A | 8/1996 | Swerdloff et al. |
| 5,552,605 A | 9/1996 | Arata |
| 5,579,358 A | 11/1996 | Lin |
| 5,596,619 A | 1/1997 | Carol |
| 5,596,653 A | 1/1997 | Kurokawa |
| 5,621,779 A | 4/1997 | Hughes et al. |
| 5,622,187 A | 4/1997 | Carol |
| 5,625,663 A | 4/1997 | Swerdloff et al. |
| 5,647,663 A | 7/1997 | Holmes |
| 5,651,043 A | 7/1997 | Tsuyuki et al. |
| 5,661,773 A | 8/1997 | Swerdloff et al. |
| 5,668,371 A | 9/1997 | Deasy et al. |
| 5,673,300 A | 9/1997 | Reckwerdt et al. |
| 5,692,507 A | 12/1997 | Seppi et al. |
| 5,712,482 A | 1/1998 | Gaiser et al. |
| 5,724,400 A | 3/1998 | Swerdloff et al. |
| 5,751,781 A | 5/1998 | Brown et al. |
| 5,754,622 A | 5/1998 | Hughes |
| 5,754,623 A | 5/1998 | Seki |
| 5,760,395 A | 6/1998 | Johnstone |
| 5,818,902 A | 10/1998 | Yu |
| 5,823,192 A | 10/1998 | Kalend et al. |
| 5,835,562 A | 11/1998 | Ramsdell et al. |
| 5,870,697 A | 2/1999 | Chandler et al. |
| 5,986,274 A | 11/1999 | Akiyama et al. |
| 6,038,283 A | 3/2000 | Carol et al. |
| 6,049,587 A | 4/2000 | Leksell et al. |
| 6,222,905 B1 | 4/2001 | Yoda et al. |
| 6,241,670 B1 | 6/2001 | Nambu |
| 6,260,005 B1 | 7/2001 | Yang et al. |
| 6,301,329 B1 | 10/2001 | Surridge |
| 6,345,114 B1 | 2/2002 | Mackie et al. |
| 6,360,116 B1 | 3/2002 | Jackson, Jr. et al. |
| 6,385,286 B1 | 5/2002 | Fitchard et al. |
| 6,385,288 B1 | 5/2002 | Kanematsu |
| 6,393,096 B1 | 5/2002 | Carol et al. |
| 6,438,202 B1 | 8/2002 | Olivera et al. |
| 6,473,490 B1 | 10/2002 | Siochi |
| 6,477,229 B1 | 11/2002 | Grosser |
| 6,510,199 B1 | 1/2003 | Hughes et al. |
| 6,560,311 B1 | 5/2003 | Shepard et al. |
| 6,661,870 B2 | 12/2003 | Kapatoes et al. |
| 6,697,452 B2 | 2/2004 | Xing |
| 6,719,683 B2 | 4/2004 | Frohlich |
| 6,741,674 B2 | 5/2004 | Lee |
| 6,757,355 B1 | 6/2004 | Siochi |
| 6,792,073 B2 | 9/2004 | Deasy et al. |
| 6,792,074 B2 | 9/2004 | Erbel et al. |
| 6,810,107 B2 | 10/2004 | Steinberg |
| 6,842,502 B2 | 1/2005 | Jaffray et al. |
| 6,853,702 B2 | 2/2005 | Renner |
| 6,882,702 B2 | 4/2005 | Luo |
| 6,904,125 B2 | 6/2005 | Van Dyk et al. |
| 6,915,005 B1 | 7/2005 | Ruchala et al. |
| 6,963,771 B2 | 11/2005 | Scarantino et al. |
| 7,046,831 B2 | 5/2006 | Ruchala et al. |
| 7,084,410 B2 | 8/2006 | Beloussov et al. |
| 7,186,991 B2 | 3/2007 | Kato et al. |
| 7,187,752 B2 | 3/2007 | Kotler et al. |
| 7,221,733 B1* | 5/2007 | Takai et al. .............. 378/65 |
| 7,367,955 B2 | 5/2008 | Zhang et al. |
| 7,391,026 B2 | 6/2008 | Trinkaus et al. |
| 7,412,029 B2 | 8/2008 | Myles |
| 7,450,687 B2 | 11/2008 | Yeo et al. |
| 7,492,858 B2 | 2/2009 | Partain et al. |
| 7,496,173 B2 | 2/2009 | Goldman et al. |
| 7,519,150 B2 | 4/2009 | Romesberg, III et al. |
| 7,567,694 B2 | 7/2009 | Lu et al. |
| 7,574,251 B2* | 8/2009 | Lu et al. .............. 600/427 |
| 7,609,809 B2 | 10/2009 | Kapatoes et al. |
| 7,611,452 B2 | 11/2009 | Allison et al. |
| 7,639,853 B2* | 12/2009 | Olivera et al. .............. 382/128 |
| 7,639,854 B2* | 12/2009 | Schnarr et al. .............. 382/128 |
| 7,643,661 B2 | 1/2010 | Ruchala et al. |
| 7,773,788 B2* | 8/2010 | Lu et al. .............. 382/128 |
| 7,945,022 B2 | 5/2011 | Nelms et al. |
| 2002/0091315 A1* | 7/2002 | Spetz .............. 600/407 |
| 2002/0193685 A1 | 12/2002 | Mate et al. |
| 2003/0048868 A1 | 3/2003 | Bailey et al. |
| 2003/0212325 A1 | 11/2003 | Cotrutz et al. |
| 2004/0068182 A1 | 4/2004 | Misra |
| 2004/0096033 A1 | 5/2004 | Seppi et al. |
| 2004/0165696 A1 | 8/2004 | Lee |
| 2004/0254448 A1 | 12/2004 | Amies et al. |
| 2005/0020917 A1* | 1/2005 | Scherch .............. 600/437 |
| 2005/0080332 A1 | 4/2005 | Shiu et al. |
| 2005/0096515 A1 | 5/2005 | Geng |
| 2005/0111621 A1* | 5/2005 | Riker et al. .............. 378/65 |
| 2005/0143965 A1 | 6/2005 | Failla et al. |
| 2005/0197564 A1 | 9/2005 | Dempsey |
| 2005/0201516 A1* | 9/2005 | Ruchala et al. .............. 378/65 |
| 2005/0251029 A1 | 11/2005 | Khamene et al. |
| 2006/0078086 A1 | 4/2006 | Riley et al. |
| 2006/0153330 A1 | 7/2006 | Wong et al. |
| 2006/0241332 A1 | 10/2006 | Klein et al. |
| 2006/0285639 A1 | 12/2006 | Olivera et al. |
| 2006/0285640 A1 | 12/2006 | Nizin et al. |
| 2007/0041495 A1* | 2/2007 | Olivera et al. .............. 378/65 |
| 2007/0041496 A1* | 2/2007 | Olivera et al. .............. 378/65 |
| 2007/0041497 A1* | 2/2007 | Schnarr et al. .............. 378/65 |
| 2007/0041498 A1 | 2/2007 | Olivera et al. |
| 2007/0041499 A1* | 2/2007 | Lu et al. .............. 378/65 |
| 2007/0041500 A1* | 2/2007 | Olivera et al. .............. 378/65 |
| 2007/0043286 A1* | 2/2007 | Lu et al. .............. 600/407 |
| 2007/0076846 A1* | 4/2007 | Ruchala et al. .............. 378/65 |
| 2007/0127790 A1 | 6/2007 | Lau et al. |
| 2007/0156453 A1 | 7/2007 | Frielinghaus et al. |
| 2007/0195929 A1* | 8/2007 | Ruchala et al. .............. 378/65 |
| 2007/0197908 A1 | 8/2007 | Ruchala et al. |
| 2008/0002809 A1 | 1/2008 | Bodduluri |
| 2008/0002811 A1 | 1/2008 | Allison |
| 2008/0008291 A1* | 1/2008 | Alakuijala et al. .............. 378/65 |
| 2008/0031406 A1 | 2/2008 | Yan et al. |
| 2008/0049896 A1 | 2/2008 | Kuduvalli |
| 2008/0064953 A1 | 3/2008 | Falco |
| 2008/0193006 A1 | 8/2008 | Udupa et al. |
| 2008/0247510 A1* | 10/2008 | Gertner et al. .............. 378/65 |
| 2008/0279328 A1 | 11/2008 | Zeitler et al. |
| 2009/0041200 A1* | 2/2009 | Lu et al. .............. 378/152 |
| 2009/0052623 A1* | 2/2009 | Tome et al. .............. 378/65 |
| 2009/0116616 A1* | 5/2009 | Lu et al. .............. 378/65 |
| 2009/0154644 A1* | 6/2009 | Nord et al. .............. 378/65 |
| 2009/0252291 A1* | 10/2009 | Lu et al. .............. 378/65 |
| 2010/0053208 A1 | 3/2010 | Menningen et al. |
| 2010/0054413 A1 | 3/2010 | Sobering et al. |
| 2010/0119032 A1* | 5/2010 | Yan et al. .............. 378/4 |
| 2010/0228116 A1* | 9/2010 | Lu et al. .............. 600/411 |
| 2011/0019889 A1* | 1/2011 | Gering et al. .............. 382/131 |
| 2011/0112351 A1 | 5/2011 | Fordyce et al. |

FOREIGN PATENT DOCUMENTS

| | | |
|---|---|---|
| JP | 2001340474 | 12/2001 |
| JP | 2002210029 | 7/2002 |
| JP | 2002522129 | 7/2002 |
| JP | 2004166975 | 6/2004 |
| JP | 2005160804 | 6/2005 |
| JP | 2005518908 | 6/2005 |
| WO | 9014129 | 11/1990 |
| WO | 0007669 | 2/2000 |
| WO | 03076003 | 9/2003 |
| WO | 03092789 | 11/2003 |
| WO | 2004105574 | 12/2004 |
| WO | 2005057463 | 6/2005 |

OTHER PUBLICATIONS

Purdy, James, "3D Treatment Planning and Intensity-Modulated Radiation Therapy," Oncology, vol. 13, No. 10, suppl. 5 (Oct. 1999).

Bert, Christoph, et al., "4D Treatment Planning for Scanned Ion Beams", BioMed Central, Radiation Oncology, 2:24, available online at: <http://www.ro-journal.com/content/2/1/24>, 2007.

Bertalmio, Marcelo, et al., "Morphing Active Contours", IEEE Transactions on Pattern Analysis and Machine Intelligence, vol. 22, No. 7, pp. 733-737, Jul. 2000.

Yu, Cedric X., et al., "A Method for Implementing Dynamic Photon Beam Intensity Modulation using Independent Jaws and a Multileaf Collimator," Phys. Med. Biol. 40. 1995: 769-787.

Lee, Jason et al., "Intensity Modulated Radiation Therapy; An Introduction for Patients and Clinicians," www.oncolink.com/templates/treatment/article.cfm?c=45&s=33&id=182; Jun. 16, 2001.

Keall, Paul, "4-Dimensional Computed Tomography Imaging and Treatment Planning," Seminars in Radiation Oncology, vol. 14, No. 1, Jan. 2004; pp. 81-90.

Lof, J. et al., "An Adaptive Control Algorithm for Optimization of Intensity Modulated Radiotherapy Considering Uncertainties in Beam Profiles, Patient Set-Up and Internal Organ Motion", Physics in Medicine and Biology 43, 1605-1628, Printed in the UK, 1998.

Lu, W., et al., "Automatic Re-Contouring Regions of Interest Based on Deformable Registration and Surface Reconstruction," AAPM 2004, (abstract: Medical Physics 31, 1845-6).

Lu, W., et al., "Automatic Re-Contouring in 4D Radiotherapy", Physical Medical Biology, Mar. 7, 2006, 51 (5):1077-99.

Lu, W., et al., 2004 "Automatic Re-Contouring for 4-D Planning and Adaptive Radiotherapy," The 90th RSNA Meeting, Chicago, Illinois, (abstract:Radiology 227 (p.) 543).

Mackie, T. Rockwell et al., "Tomotherapy" Seminars in Radiation Oncology, vol. 9, No. 1, Jan. 1, 1999, pp. 108-117, XP002603992.

Rogus, Ronald, D., "Accuracy of a Photogrammetry-Based Patient Positioning and Monitoring System for Radiation Therapy", Medical Physics Online, available online at: <http://scitation.aip.org/vsearch/servlet/VerityServlet?KEY=FREESR&smode=strresults &sort=chron&maxdisp=25&threshold=0 &possible1=Ronald+Rogus&possible1zone=article &OUTLOG=NO&viewabs=MPHYA6&key=DISPLAY&docID=2 &page=1&chapter=0>, abstract view, vol. 26, issue 5, 2 pages, May 1999.

Ruchala, Kenneth, et al., "Adaptive IMRT with Tomotherapy", RT Image, vol. 14, No. 25, pp. 14-18, Jun. 18, 2001.

Rueckert, D. et al., "Nonrigid Registration Using Free-Form Deformations: Application to Breast MR Images", IEEE Transactions on Medical Imaging, vol. 18, No. 8, pp. 712-721, Aug. 1999.

Young, Yuan-Nan, et al., "Registration-Based Morphing of Active Contours for Segmentation of CT Scans", Mathematical Biosciences and Engineering, vol. 2, No. 1, pp. 79-96, Jan. 2005.

Office Action from Chinese Patent Office for Application No. 200880110753.0 dated Jul. 5, 2011.

PCT/US2008/081300 International Search Report and Written Opinion, 12 pages, dated May 18, 2009.

\* cited by examiner

METHOD FOR ADAPTING FRACTIONATION OF A RADIATION THERAPY DOSE

RELATED APPLICATIONS

This application claims priority to U.S. Provisional Patent Application No. 60/982,448, filed on Oct. 25, 2007, titled ADAPTIVE FRACTIONATION, the entire contents of which are incorporated herein by reference.

BACKGROUND

Radiation therapy treatment devices deliver radiation to a patient in multiple treatments, each of which is called a fraction. In conventional fractionated therapy (FT), a standard radiation therapy protocol, the total prescribed dose of radiation is divided into equal fraction sizes that are delivered to a patient at discrete times over the course of treatment (e.g., over a period of weeks rather than in a single session). The purpose of fractionation is to increase normal tissue sparing while simultaneously maintaining the same level of tumor cell kill, thereby increasing the therapeutic ratio. Fractionation therapy usually results in a better therapeutic ratio than single session therapy because it spares more normal tissue through repair of sub-lethal damage between dose fractions and repopulation of cells. Concurrently, FT increases tumor damage through reoxygenation and redistribution of tumor cells. The number of fractions and resulting dose per fraction are determined during the planning procedure prior to treatment in conventional FT. A typical radiotherapy treatment course consists of 30 to 40 fractions, with the predetermined fraction size (e.g., 2 Gy/fraction) used throughout the treatment.

SUMMARY

Conventional fractionation therapy does not take into account the variations of the relative positions between sensitive structure(s) (organ(s) at risk, OAR) and the tumor, which occur over the course of treatment. There are many sources of inter-fraction variations of internal structures that can occur during a course of a patient's treatment. These variations can be attributable to physiological changes in the patient. Examples of such variations occur when the patient has daily variations in rectal and bladder filling, the patient loses or gains weight, or when the tumor regresses during therapy. The variations are usually considered errors, but tools such as margin and/or other motion compensation techniques can be used to create a robust treatment plan.

Over the past decades, improvements in computers, radiation treatment planning software, and medical imaging modalities have been incorporated into radiation therapy practice. These improvements have led to the development of image guided radiation therapy (IGRT). With state of the art development of IGRT, inter-fraction changes of the tumor and the OAR can be well quantified. Adapting the fractions planned for a patient can take advantage of such OAR and tumor relative position changes or configurations to provide the same total dose to the tumor and still minimize the dose received by the OAR. Consequently, a better therapeutic ratio may be achieved by using a varied or adaptive fraction size, as compared to a constant fraction size, over the course of treatment.

In general, the invention relates to a method of adapting a treatment plan for a patient by varying the fraction size given on any individual day, based on the use of daily patient registration (i.e., taking images of the patient before each fraction is delivered to see the position and size of the tumor on that day). According to the invention, the fraction size can be dynamically altered based upon the biology of the tumor. To put it another way, the oncologist can consider the biological effect in optimizing the fraction size on any given day (maybe some days the tumor has moved farther away from healthy tissue so more radiation can be safely given, while on other days, maybe less radiation should be delivered for one reason or another).

The key to optimizing the therapeutic ratio by adapting fractionation is in the time-varying distances between the OAR and the tumor. These time-varying distances can be measured or detected via one or more imaging modalities at any point before and/or during the course of treatment. The distance between the OAR and the tumor determines the OAR/tumor dose ratio—the larger the distance, the smaller the dose ratio. The fraction size can then be adapted to deliver more or larger doses when the ratio is smaller, and fewer or smaller doses when the ratio is larger. In other words, a higher or lower dose can be delivered at each treatment interval based on the configuration favoring or disfavoring the dose delivery to the tumor and not to the OAR. In this way, the desired tumor cell kill can be achieved while OAR sparing is improved.

In one embodiment, the invention provides a method of adapting a treatment plan. The method includes preparing a treatment plan for a patient, the treatment plan including multiple treatment fractions each having a planned delivered dose. The method also includes acquiring an image of the patient prior to delivering any one of the treatment fractions, and adjusting the treatment plan for the patient prior to delivering the one treatment fraction, wherein adjusting the treatment plan for the patient comprises increasing or decreasing the dose to be delivered during the treatment fraction based upon the information acquired.

In another embodiment the invention provides a method of treating a patient with radiation therapy using a plurality of fractions to deliver a total planned radiation dose to a tumor volume that has a sensitive structure in physical proximity to a tumor volume. The method comprises preparing a treatment plan for a patient, the treatment plan including multiple treatment fractions each having a planned delivered dose, acquiring an image of the patient, using the acquired information to adjust the dose to be delivered for a given treatment fraction, and delivering radiation to the patient according to the treatment plan such that the adjusted dose is delivered to the patient.

Other aspects of the invention will become apparent by consideration of the detailed description and accompanying drawings.

DETAILED DESCRIPTION

Figure 1:
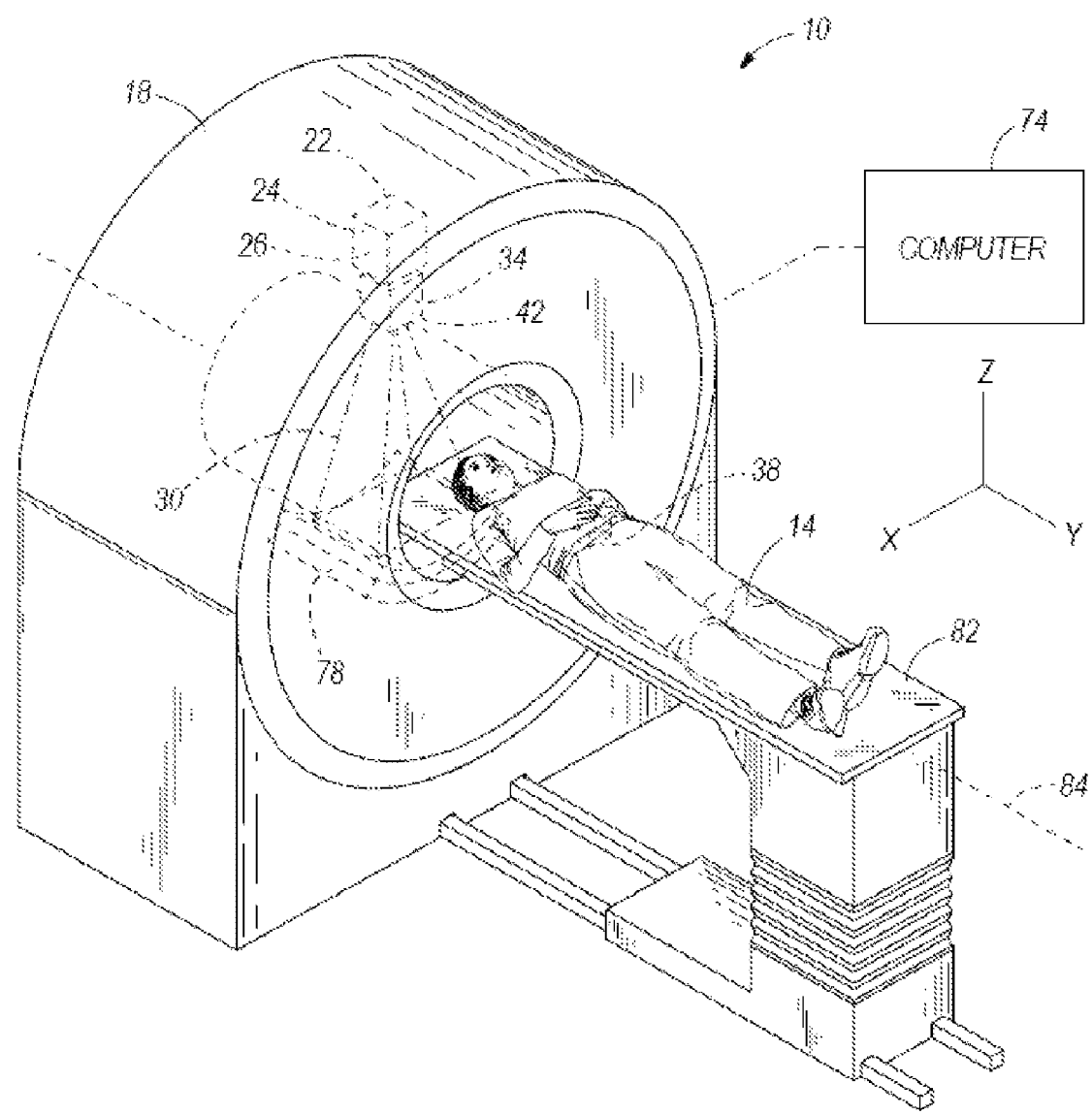
FIG. 1 is a perspective view of a radiation therapy treatment system.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings.

Although directional references, such as upper, lower, downward, upward, rearward, bottom, front, rear, etc., may be made herein in describing the drawings, these references are made relative to the drawings (as normally viewed) for convenience. These directions are not intended to be taken literally or limit the present invention in any form. In addition, terms such as "first," "second," and "third" are used herein for purposes of description and are not intended to indicate or imply relative importance or significance.

In addition, it should be understood that embodiments of the invention include hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software. As such, it should be noted that a plurality of hardware and software based devices, as well as a plurality of different structural components may be utilized to implement the invention. Furthermore, and as described in subsequent paragraphs, the specific mechanical configurations illustrated in the drawings are intended to exemplify embodiments of the invention and that other alternative mechanical configurations are possible.

FIG. 1 illustrates a radiation therapy treatment system 10 that can provide radiation therapy to a patient 14. The radiation therapy treatment can include photon-based radiation therapy, brachytherapy, electron beam therapy, proton, neutron, or particle therapy, or other types of treatment therapy. The radiation therapy treatment system 10 includes a gantry 18. The gantry 18 can support a radiation module 22, which can include a radiation source 24 and a linear accelerator 26 (a.k.a. "a linac") operable to generate a beam 30 of radiation. Though the gantry 18 shown in the drawings is a ring gantry, i.e., it extends through a full 360° arc to create a complete ring or circle, other types of mounting arrangements may also be employed. For example, a C-type, partial ring gantry, or robotic arm could be used. Any other framework capable of positioning the radiation module 22 at various rotational and/or axial positions relative to the patient 14 may also be employed. In addition, the radiation source 24 may travel in path that does not follow the shape of the gantry 18. For example, the radiation source 24 may travel in a non-circular path even though the illustrated gantry 18 is generally circular-shaped. The gantry 18 of the illustrated embodiment defines a gantry aperture 32 into which the patient 14 moves during treatment.

The radiation module 22 can also include a modulation device 34 operable to modify or modulate the radiation beam 30. The modulation device 34 provides the modulation of the radiation beam 30 and directs the radiation beam 30 toward the patient 14. Specifically, the radiation beam 30 is directed toward a portion 38 of the patient. Broadly speaking, the portion may include the entire body, but is generally smaller than the entire body and can be defined by a two-dimensional area and/or a three-dimensional volume. A portion or area desired to receive the radiation, which may be referred to as a target or target region, is an example of a region of interest. Another type of region of interest is a region at risk. If a portion includes a region at risk, the radiation beam is preferably diverted from the region at risk. Such modulation is sometimes referred to as intensity modulated radiation therapy ("IMRT").

Figure 2:
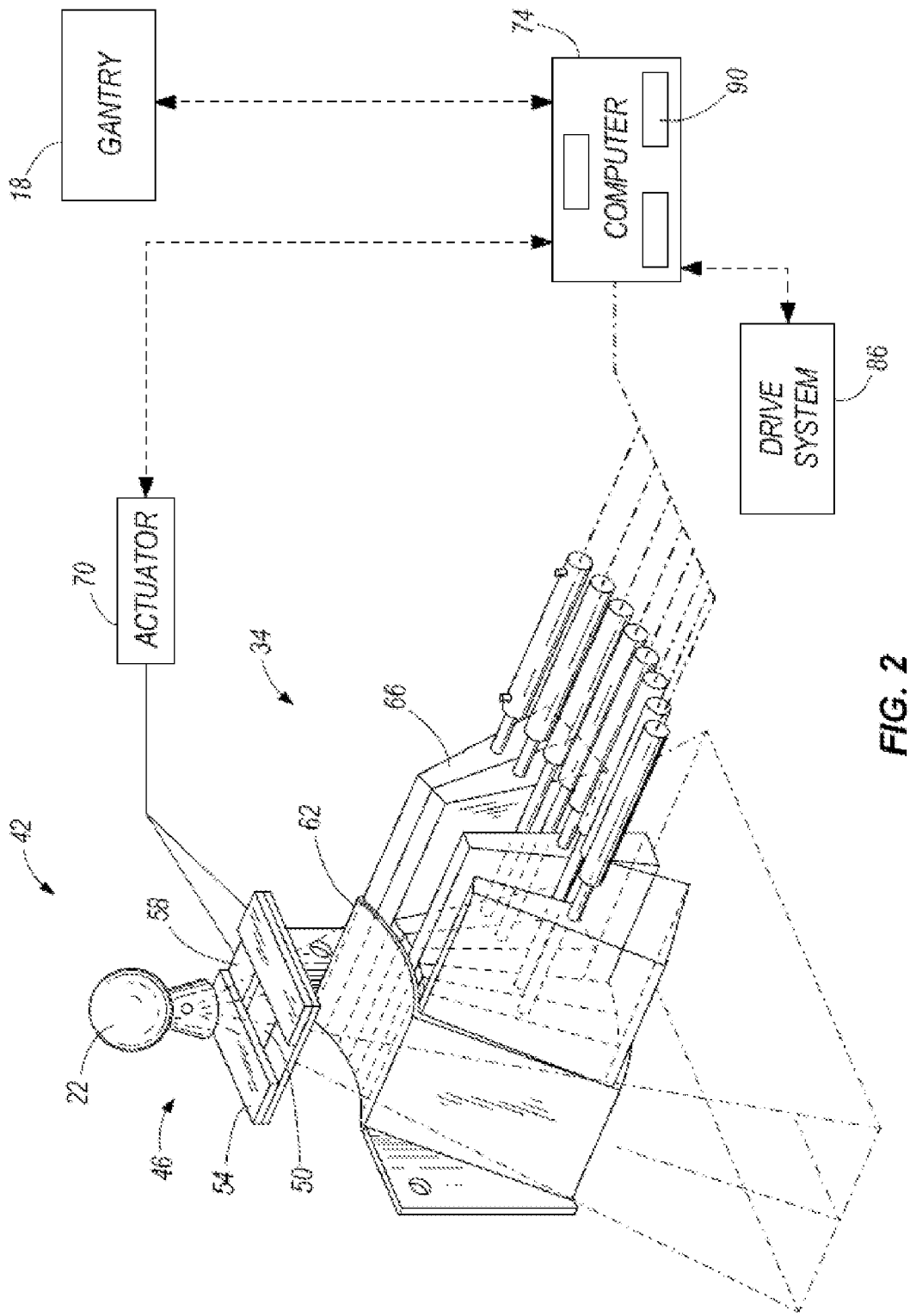
FIG. 2 is a perspective view of a multi-leaf collimator that can be used in the radiation therapy treatment system illustrated in FIG. 1.

The modulation device 34 can include a collimation device 42 as illustrated in FIG. 2. The collimation device 42 includes a set of jaws 46 that define and adjust the size of an aperture 50 through which the radiation beam 30 may pass. The jaws 46 include an upper jaw 54 and a lower jaw 58. The upper jaw 54 and the lower jaw 58 are moveable to adjust the size of the aperture 50. The position of the jaws 46 regulates the shape of the beam 30 that is delivered to the patient 14.

In one embodiment, and illustrated in FIG. 2, the modulation device 34 can comprise a multi-leaf collimator 62 (a.k.a. "MLC"), which includes a plurality of interlaced leaves 66 operable to move from position to position, to provide intensity modulation. It is also noted that the leaves 66 can be moved to a position anywhere between a minimally and maximally-open position. The plurality of interlaced leaves 66 modulate the strength, size, and shape of the radiation beam 30 before the radiation beam 30 reaches the portion 38 on the patient 14. Each of the leaves 66 is independently controlled by an actuator 70, such as a motor or an air valve so that the leaf 66 can open and close quickly to permit or block the passage of radiation. The actuators 70 can be controlled by a computer 74 and/or controller.

The radiation therapy treatment system 10 can also include a detector 78, e.g., a kilovoltage or a megavoltage detector, operable to receive the radiation beam 30, as illustrated in FIG. 1. The linear accelerator 26 and the detector 78 can also operate as a computed tomography (CT) system to generate CT images of the patient 14. The linear accelerator 26 emits the radiation beam 30 toward the portion 38 in the patient 14. The portion 38 absorbs some of the radiation. The detector 78 detects or measures the amount of radiation absorbed by the portion 38. The detector 78 collects the absorption data from different angles as the linear accelerator 26 rotates around and emits radiation toward the patient 14. The collected absorption data is transmitted to the computer 74 to process the absorption data and to generate images of the patient's body tissues and organs. The images can also illustrate bone, soft tissues, and blood vessels. The system 10 can also include a patient support device, shown as a couch 82, operable to support at least a portion of the patient 14 during treatment. While the illustrated couch 82 is designed to support the entire body of the patient 14, in other embodiments of the invention the patient support need not support the entire body, but rather can be designed to support only a portion of the patient 14 during treatment. The couch 82 moves into and out of the field of radiation along an axis 84 (i.e., Y axis). The couch 82 is also capable of moving along the X and Z axes as illustrated in FIG. 1.

Figure 3:
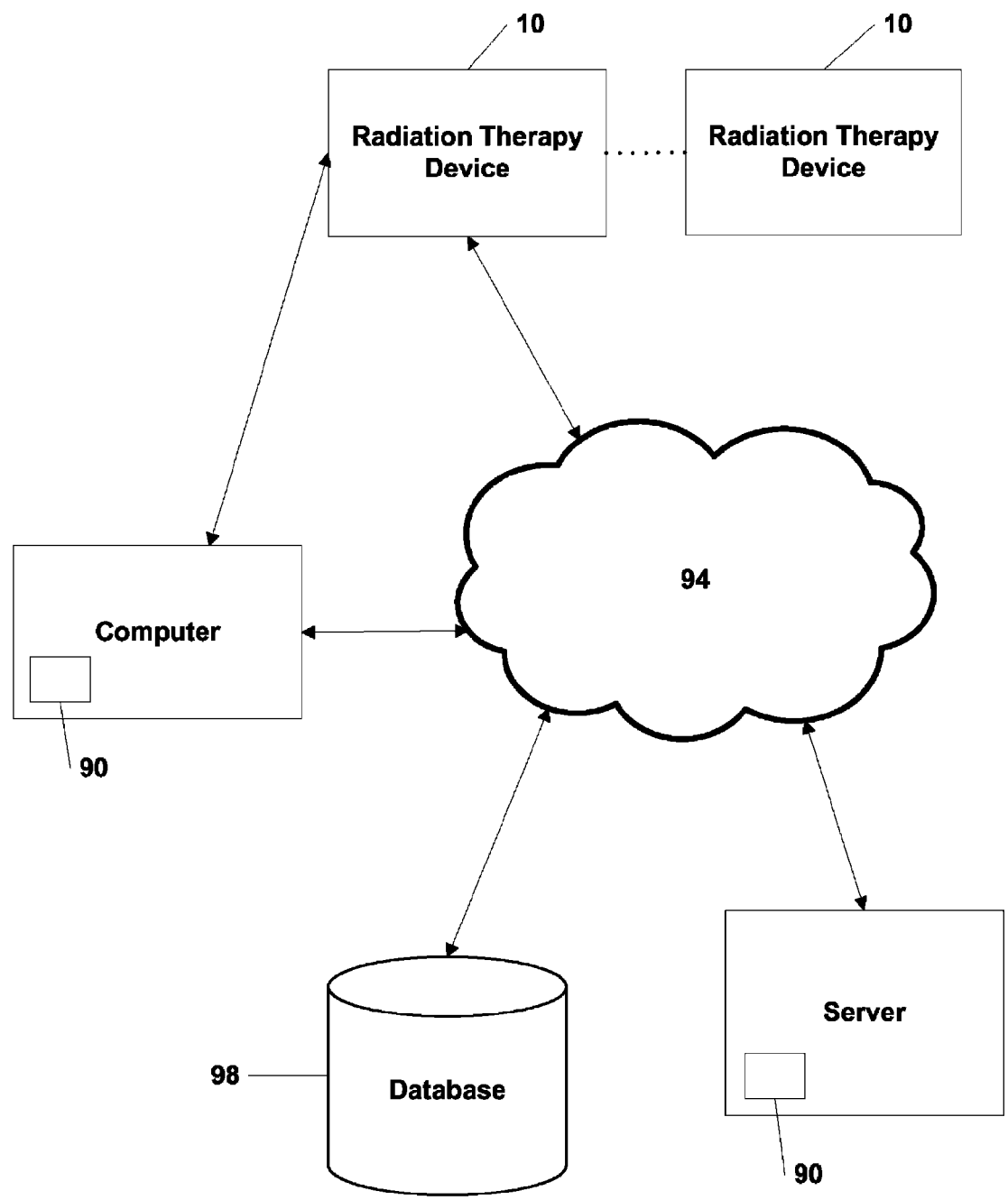
FIG. 3 is a schematic illustration of the radiation therapy treatment system of FIG. 1.

The computer 74, illustrated in FIGS. 2 and 3, includes an operating system for running various software programs and/or a communications application. In particular, the computer 74 can include a software program(s) 90 that operates to communicate with the radiation therapy treatment system 10. The computer 74 can include any suitable input/output device adapted to be accessed by medical personnel. The computer 74 can include typical hardware such as a processor, I/O interfaces, and storage devices or memory. The computer 74 can also include input devices such as a keyboard and a mouse. The computer 74 can further include standard output devices, such as a monitor. In addition, the computer 74 can include peripherals, such as a printer and a scanner.

The computer 74 can be networked with other computers 74 and radiation therapy treatment systems 10. The other computers 74 may include additional and/or different computer programs and software and are not required to be identical to the computer 74, described herein. The computers 74 and radiation therapy treatment system 10 can communicate with a network 94. The computers 74 and radiation therapy treatment systems 10 can also communicate with a database(s) 98 and a server(s) 102. It is noted that the software program(s) 90 could also reside on the server(s) 102.

The network 94 can be built according to any networking technology or topology or combinations of technologies and topologies and can include multiple sub-networks. Connections between the computers and systems shown in FIG. 3 can be made through local area networks ("LANs"), wide area networks ("WANs"), public switched telephone networks ("PSTNs"), wireless networks, Intranets, the Internet, or any other suitable networks. In a hospital or medical care facility, communication between the computers and systems shown in FIG. 3 can be made through the Health Level Seven ("HL7") protocol or other protocols with any version and/or other required protocol. HL7 is a standard protocol which specifies the implementation of interfaces between two computer applications (sender and receiver) from different vendors for electronic data exchange in health care environments. HL7 can allow health care institutions to exchange key sets of data from different application systems. Specifically, HL7 can define the data to be exchanged, the timing of the interchange, and the communication of errors to the application. The formats are generally generic in nature and can be configured to meet the needs of the applications involved.

Communication between the computers and systems shown in FIG. 3 can also occur through the Digital Imaging and Communications in Medicine (DICOM) protocol with any version and/or other required protocol. DICOM is an international communications standard developed by NEMA that defines the format used to transfer medical image-related data between different pieces of medical equipment. DICOM RT refers to the standards that are specific to radiation therapy data.

The two-way arrows in FIG. 3 generally represent two-way communication and information transfer between the network 94 and any one of the computers 74 and the systems 10 shown in FIG. 3. However, for some medical and computerized equipment, only one-way communication and information transfer may be necessary.

Figure 4:
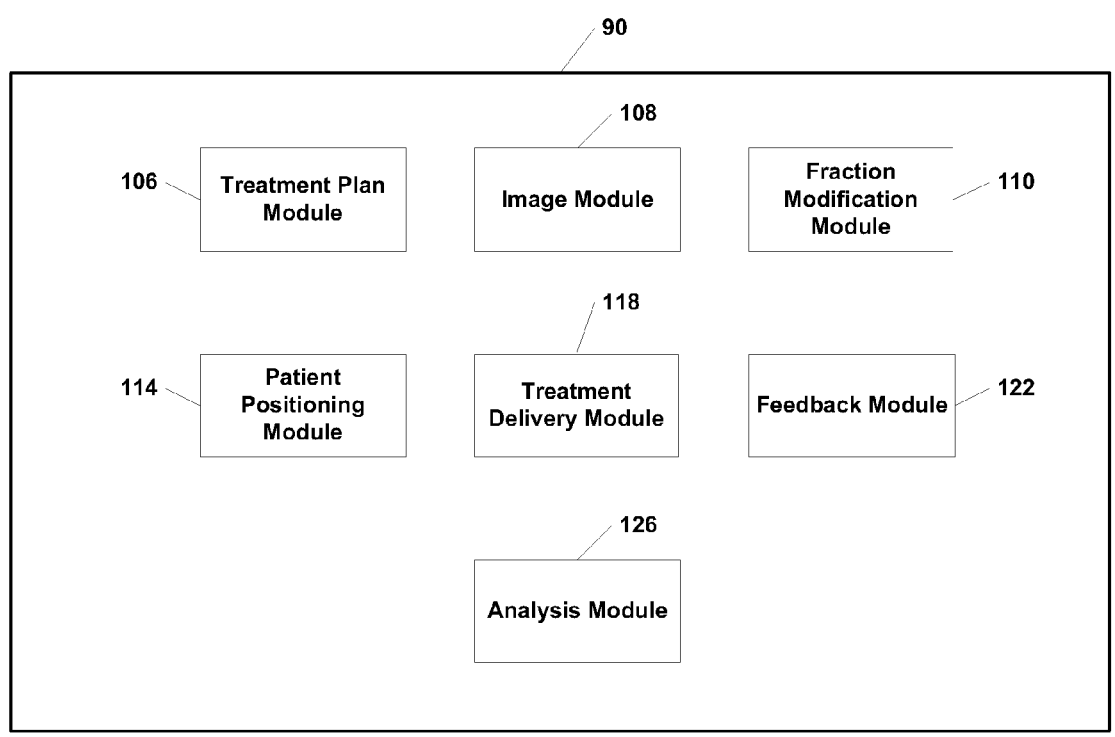
FIG. 4 is a schematic diagram of a software program used in the radiation therapy treatment system.

The software program 90 (illustrated in block diagram form in FIG. 4) includes a plurality of modules that communicate with one another to perform functions of the radiation therapy treatment process. The various modules also communicate with one another to determine if delivery of the radiation therapy treatment plan occurred as intended.

The software program 90 includes a treatment plan module 106 operable to generate a treatment plan for the patient 14 based on data input to the system 10 by medical personnel. The data includes one or more images (e.g., planning images and/or pre-treatment images) of at least a portion of the patient 14. The treatment plan module 106 separates the treatment into a plurality of fractions and determines the radiation dose for each fraction or treatment based on the prescription input by medical personnel. The treatment plan module 106 also determines the radiation dose for the portion 38. The radiation dose can be based on various contours drawn around the portion 38 that define the margin around the portion 38. Multiple portions 38 may be present and included in the same treatment plan.

The software program 90 also includes an image module 108 operable to acquire images of at least a portion of the patient 14. The image module 108 can instruct the on-board image device, such as a CT imaging device to acquire images of the patient 14 before treatment commences, during treatment, and after treatment according to desired protocols. In one aspect, the image module 108 acquires an image of the patient 14 while the patient 14 is substantially in a treatment position. Other off-line imaging devices or systems may be used to acquire pre-treatment images of the patient 14, such as non-quantitative CT, MRI, PET, SPECT, ultrasound, transmission imaging, fluoroscopy, RF-based localization, and the like. The acquired pre-treatment image(s) can be used for registration of the patient 14 and/or to generate a deformation map to identify the differences between one or more of the planning images and one or more of the pre-treatment, during-treatment, or after-treatment images.

The acquired images also can be used for registration of the patient 14 and/or to determine or predict a radiation dose to be delivered to the patient 14. The acquired images also can be used to determine a radiation dose that the patient 14 received during prior treatments or fractions. The image module 108 also is operable to acquire images of at least a portion of the patient 14 while the patient is receiving treatment to determine a radiation dose that the patient 14 is receiving in real-time.

The software program 90 also includes a fraction modification module 110 operable to determine parameters for each fraction. Each fraction to be delivered can be modified prior to delivery of treatment and/or during delivery of the treatment. Additional details on the modification of a fraction are discussed below.

The software program 90 also includes a patient positioning module 114 operable to position and align the patient 14 with respect to the isocenter of the gantry 18 for a particular treatment fraction. While the patient is on the couch 82, the patient positioning module 114 acquires an image of the patient 14 and compares the current position of the patient 14 to the position of the patient in a reference image. The reference image can be a planning image, any pre-treatment image, or a combination of a planning image and a pre-treatment image. If the patient's position needs to be adjusted, the patient positioning module 114 provides instructions to the drive system 86 to move the couch 82 or the patient 14 can be manually moved to the new position. In one construction, the patient positioning module 114 can receive data from lasers positioned in the treatment room to provide patient position data with respect to the isocenter of the gantry 18. Based on the data from the lasers, the patient positioning module 114 provides instructions to the drive system 86, which moves the couch 82 to achieve proper alignment of the patient 14 with respect to the gantry 18. It is noted that devices and systems, other than lasers, can be used to provide data to the patient positioning module 114 to assist in the alignment process.

The patient positioning module 114 also is operable to detect and/or monitor patient motion during treatment. The patient positioning module 114 may communicate with and/or incorporate a motion detection system 112, such as x-ray, in-room CT, laser positioning devices, camera systems, spirometers, ultrasound, tensile measurements, chest bands, and the like. The patient motion can be irregular or unexpected, and does not need to follow a smooth or reproducible path.

The patient positioning module 114 also is operable to identify a position of a first structure relative to a second structure prior to delivery of the treatment plan. The positioning module 114 can utilize internal landmarks such as fiducial markers to identify the relative positions of the structures. The positioning module 114 can also utilize surrogates to identify the relative positions of the structures. Surrogates can include a respiration monitor that detects air flow in response to lung movement, skin markers (measured by a camera), and seeds (e.g., radioactive or electromagnetic seeds or radiooptical seeds).

The software program 90 also includes a treatment delivery module 118 operable to instruct the radiation therapy treatment system 10 to deliver the fraction to the patient 14 according to the treatment plan. The treatment delivery module 118 can generate and transmit instructions to the gantry 18, the linear accelerator 26, the modulation device 34, and the drive system 86 to deliver radiation to the patient 14. The instructions coordinate the necessary movements of the gantry 18, the modulation device 34, and the drive system 86 to deliver the radiation beam 30 to the proper target in the proper amount as specified in the treatment plan.

The treatment delivery module 118 also calculates the appropriate pattern, position, and intensity of the radiation beam 30 to be delivered, to match the prescription as specified by the treatment plan. The pattern of the radiation beam 30 is generated by the modulation device 34, and more particularly by movement of the plurality of leaves in the multi-leaf collimator. The treatment delivery module 118 can utilize canonical, predetermined or template leaf patterns to generate the appropriate pattern for the radiation beam 30 based on the treatment parameters. The treatment delivery module 118 can also include a library of patterns for typical cases that can be accessed in which to compare the present patient data to determine the pattern for the radiation beam 30.

The software program 90 also includes a feedback module 122 operable to receive data from the radiation therapy treatment system 10 during a patient treatment. The feedback module 122 can receive data from the radiation therapy treatment device and can include information related to patient transmission data, ion chamber data, MLC data, system temperatures, component speeds and/or positions, flow rates, etc. The feedback module 122 can also receive data related to the treatment parameters, amount of radiation dose the patient received, image data acquired during the treatment, and patient movement. In addition, the feedback module 122 can receive input data from a user and/or other sources. The feedback module 122 acquires and stores the data until needed for further processing.

The software program 90 also includes an analysis module 126 operable to analyze the data from the feedback module 122 to determine whether delivery of the treatment plan occurred as intended and to validate that the planned delivery is reasonable based on the newly-acquired data. The analysis module 126 can also determine, based on the received data and/or additional inputted data, whether a problem has occurred during delivery of the treatment plan. For example, the analysis module 126 can determine if the problem is related to an error of the radiation therapy treatment device 10, an anatomical error, such as patient movement, and/or a clinical error, such as a data input error. The analysis module 126 can detect errors in the radiation therapy treatment device 10 related to the couch 82, the device output, the gantry 18, the multi-leaf collimator 62, the patient setup, and timing errors between the components of the radiation therapy treatment device 10. For example, the analysis module 126 can determine if a couch replacement was performed during planning, if fixation devices were properly used and accounted for during planning, if position and speed is correct during treatment. The analysis module 126 can determine whether changes or variations occurred in the output parameters of the radiation therapy treatment device 10. With respect to the gantry 18, the analysis module 126 can determine if there are errors in the speed and positioning of the gantry 18. The analysis module 126 can receive data to determine if the multi-leaf collimator 62 is operating properly. For example, the analysis module 126 can determine if the leaves 66 move at the correct times, if any leaves 66 are stuck in place, if leaf timing is properly calibrated, and whether the leaf modulation pattern is correct for any given treatment plan. The analysis module 126 also can validate patient setup, orientation, and position for any given treatment plan. The analysis module 126 also can validate that the timing between the gantry 18, the couch 62, the linear accelerator 26, the leaves 66 are correct.

The analysis module 126 can also utilize deformable registration data to ensure that the patient 14 is receiving the correct radiation dose across multiple fractions. When analyzing the doses, it is useful to accumulate the dose across multiple treatment fractions to determine if any errors are being exacerbated or if they are mitigating each other. Registration is a method for determining the correlation between locations of a patient's anatomy or physiology across multiple images. Deformable registration is a method of determining the correlation between locations of a patient's anatomy or physiology to account for non-rigid changes in anatomy between the images, phases, or times. The radiation dose delivered to the patient 14 is recalculated based upon on-line images and feedback from the radiation therapy treatment device 10 to ensure that the correct dose has been or is being delivered to the patient 14.

The analysis module 126 also can utilize data related to deformation-based contouring of images for quality assurance purposes. Deformable registration techniques can be used to generate automatic or semi-automatic contours for new images. Generally, a contour set has been defined for planning or other baseline patient images, but with new images, a contour set is not usually readily available. Rather than require an operator to manually contour the image, it can be both faster and more consistent to perform a deformable image registration, and then use the deformation results as the basis for modifying the original contour set to reflect the new patient anatomy. A similar family of template-based contouring algorithms has been developed to generate contours for newly available images, based upon previously available sets of images and contours. These template-based algorithms might contour a new patient image based upon a previous patient image and contour, or potentially based upon a canonical or atlas patient image and contour. This can be performed for adaptive therapy as a means to accumulate doses in daily images, each with automatic daily contours. Moreover, whereas previously these algorithms were used in the context of generating new contours based upon canonical or atlas images, it is a new aspect of this invention to apply these techniques to the particular wealth of image data and types of images that arise during image-guided radiotherapy. Specifically, this includes deformation and template-based contouring of multiple images of the same patient in which contour sets might only exist for one of the images. These multiple images of the patient may arise from use of an on-line or in-room patient imaging system, with images potentially taken on different days, or these images might derive from a "4D" imaging system such as a CT scanner, in which each image represents a phase of motion, such as a breathing phase. It should also be noted that the on-line or in-room imaging system might be the same, a similar, or a different modality from the reference image. For example, the reference image might be a CT image, whereas the on-line image could be CT, cone-beam CT, megavoltage CT, MRI, ultrasound, or a different modality. By porting these contouring techniques to the applications of quality assurance and adaptive therapy, it is possible to both save a considerable amount of time from the contouring of images, and this method can also improve the consistency of contours across multiple images of the same patient (taken at different times or representing different phases). It is known that manual contours can suffer from irreproducibility, whereas automatically generated contours can potentially be more consistent in applying the principles of an initial contour to the generation of subsequent contours.

Another benefit of the contouring process using deformable registration techniques is that the contours generated can provide a validation of the deformation process. If the generated contours closely reflect contours that one would manually draw, then it is a good indication that the deformation process is reasonable; whereas if the automatic contours are less relevant, it indicates to the user that perhaps the deformation is inappropriate, but also provides the user an opportunity to verify the manual contours to check for mistakes or inconsistencies. Another aspect of this method is that the deformation-based contours can be used as a rough-draft of the contours for the adaptive process, and manually edited to reflect the desired contours for the on-line images. When doing this, the deformation process can then be re-run, constraining the deformation map to match the initial contours to the manually-edited automatic contours, and this helps direct consistent results through the rest of the image.

The analysis module 126 also is operable to utilize deformation maps to perform dose calculations on various images for quality assurance purposes. A deformation map can be utilized to relate a plurality of images where one image is a planning image that is useful for dose calculation, and another image, such as an on-line image, has qualitative value but less direct utility for dose calculation. This relation could then be used to "remap" the more quantitative image to the qualitative shape of the on-line or less quantitative image. The resulting remapped image would be more appropriate than either of the other two images for dose calculation or quantitative applications as it would have the quantitative benefits of the first image, but with the updated anatomical information as contained in the second image. This could be useful in a variety of cases, such as where the first image (e.g., a planning image) is a CT and where the additional image lacks quantitative image values (e.g., MRI, PET, SPECT, ultrasound, or non-quantitative CT, etc. images). A similar application of this method would be to correct for geometrical distortion, imperfections, and/or incompleteness in lieu of, or in addition to, quantitative limitations. For example, a current MRI image that well represents anatomy but includes geometric distortion might be remapped to a CT image that is not distorted. Or multiple images could be used to simultaneously correct for both distortion while representing anatomical changes.

As noted above, it is important to be able to recalculate dose on patient images acquired after the planning image. Given these doses, it is also useful to accumulate these doses for multiple delivered fractions. These doses can be added based upon the location of the doses in physical space, but a better method is to incorporate deformation methods into the process so as to add doses based upon the structures that received the dose, even if the structures have changed location. However, it is possible to build upon this technology to perform novel types of adaptive therapy.

In the context of recalculating doses, there are several other aspects of this invention to improve or facilitate this process. For example, after recording any daily registrations applied to the patient, potentially based upon image-guidance, these same registrations can optionally be applied to the patient images when recalculating dose. This can be performed automatically or semi-automatically. Alternately, the dose could be recalculated with a different registration. The benefit is that by automatically using the recorded registrations, the process of recalculating the doses that were delivered is simplified and streamlined. Moreover, by having the ability to recalculate doses for different registrations, one can experiment to determine if other patient alignment protocols might have been more or less effective. And by not using the recorded registration, one can determine how the treatment would have been affected in the absence of image guidance.

The dose recalculation process also can be enhanced by the padding of incomplete images. This is because a limited-size image, whether limited in the axial plane and/or in the superior/inferior direction, can degrade the accuracy of dose calculations. A method to overcome this is to pad the limited-size image with other image data, such as from the planning image. This padding method can work for both axially or superior/inferior limited data. In addition, another method for padding superior/inferior data is to repeat the end slices of the incomplete image as necessary until the data is sufficiently large for improved dose calculation.

I. Introduction to Adaptive Fractionation Therapy

As noted above, the fraction modification module 110 is operable to determine parameters for each fraction of radiation dose to be delivered to the patient.

Adaptive fractionation therapy (AFT) is an on-line adaptive technique that incorporates variations of internal structures to achieve an optimal OAR sparing. The treatment plan can be adapted by varying the fraction size given on any individual day, based on the use of daily patient registration (i.e., taking images of the patient before each fraction is delivered to see the position and size of the tumor on that day). The fraction size can be dynamically altered based upon the biology of the tumor. To put it another way, the oncologist can consider the biological effect in optimizing the fraction size on any given day (maybe some days the tumor has moved farther away from healthy tissue so more radiation can be safely given, while on other days, maybe less radiation should be delivered for one reason or another).

The changes to the patient's internal structures are classified as different configurations according to their feasibility to the radiation delivery. A priori knowledge is used to describe the probability distribution of these configurations. The on-line processes include identifying the configuration and optimizing the current fraction size. A simple linear programming problem is used as the optimization tool.

Extensive simulations which include thousands of treatment courses with each course including 40 fractions are used to test the efficiency and robustness of the presented technique. The gains of OAR sparing depend on the variations of the OAR/tumor configuration and the bounds on the fraction size—the larger the variations and the looser the bounds, the larger the gains. For a typical 20% tumor/OAR configuration variations and [1 Gy, 3 Gy] bounds, the gains of OAR sparing are around 5-6 Gy, or 9-18%, for a fine a priori model and a prescribed dose of 80 Gy in 40 fractions. Even when a coarse a priori model is used, the gains are still as large as 4-5 Gy, or 7-16% compared to the conventional fractionation technique.

The following notations are used in this section:

N: total number of fractions

D: total prescribed dose $d_n$: the delivered tumor dose (fraction size) for the n th fraction $R_n$: the remaining dose right before the n th fraction, $$R_n = D - \sum_{1}^{n-1} d^k$$

M: total number of configurations $p_m$: probability of configuration m, $$\sum_{1}^{M} p_m = 1$$

Figure 5:
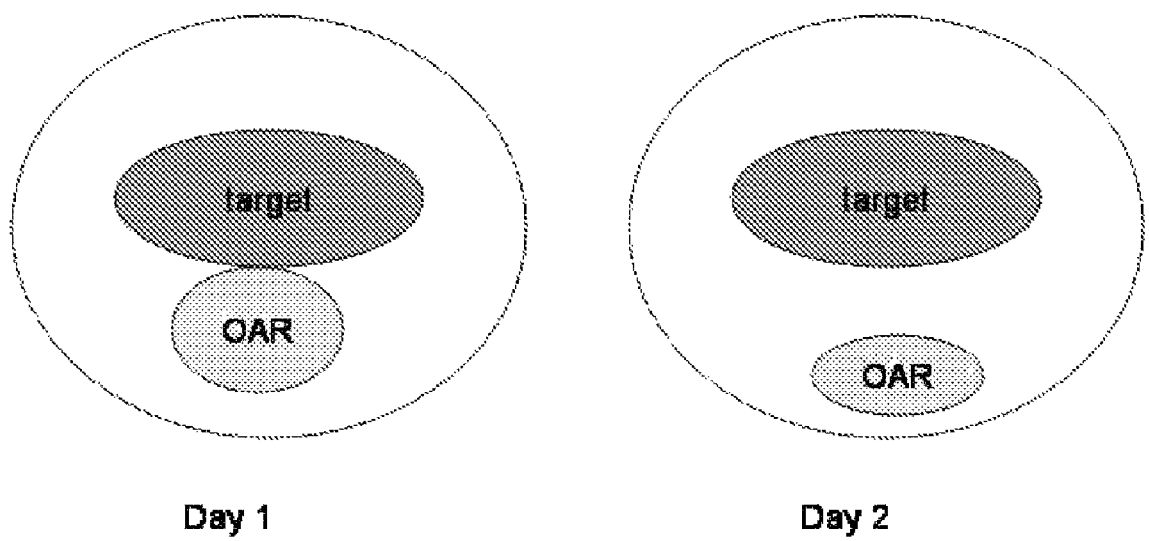
FIG. 5 illustrates the rationale for using varied fraction size in radiotherapy.

$r_m$: the ratio of OAR dose over tumor dose for configuration m, $r_1 < r_2 < \ldots < r_M$ $\underline{d}$: the prescribed lower bound fraction size $\overline{d}$: the prescribed upper bound fraction size $c_n$: the configuration for the n th fraction, $c_n \in [1,M]$ Considering that the configurations of OAR relative to the tumor position may vary from fraction to fraction, some configurations may favor radiation delivery while other configurations disfavor it. Consequently, a better OAR sparing could be achieved while maintaining the same tumor control by using a varied or adaptive fraction size. That is, intuitively, the fraction size should be increased when the OAR is positioned farther from the tumor and decreased when the OAR is positioned closer to the tumor. FIG. 5 illustrates such a rationale. On treatment day 1, the OAR is close to tumor, which disfavors the OAR sparing, while on treatment day 2, the OAR is farther away from the tumor, which favors the OAR sparing. This anatomical configuration suggests that the fraction size for day 1 should be larger than the fraction size for day 2.

Figure 6:
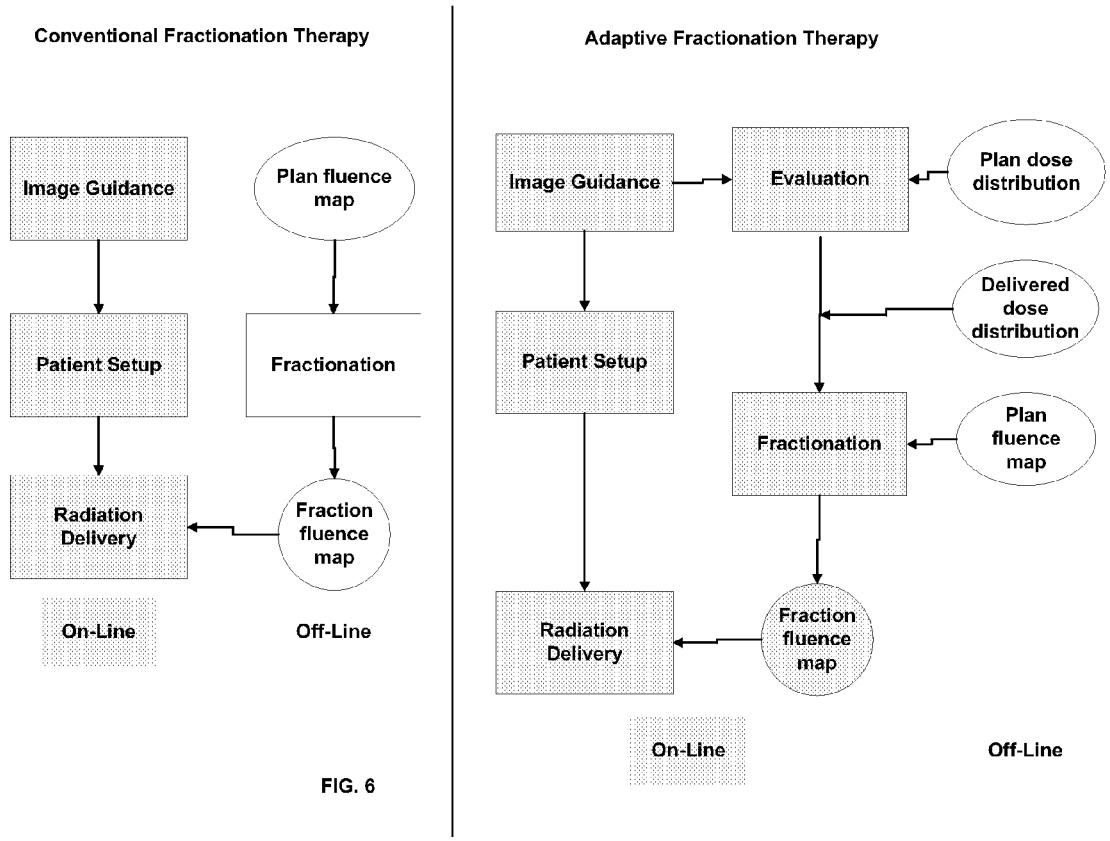
FIG. 6 illustrates flow charts comparing the processes of conventional radiotherapy delivery and adaptive fractionation radiotherapy delivery.

FIG. 6 illustrates a conventional fractionation therapy flowchart and an adaptive fractionation therapy flowchart to compare the processes involved in both techniques. In conventional FT, fractionation is performed off-line. On-line image guidance is only used for setup of the patient, ideally, to put the tumor in the treatment position. Pre-determined (mostly fixed) fraction size is used for all fractions, no matter what the daily configuration is. In AFT however, image guidance is used for patient setup and also for evaluating the anatomical configuration on treatment day. The fractionation procedure, which utilizes the daily anatomical configuration information as well as the delivered dose, is performed as an on-line process. Varied or adaptive fraction size is optimized by the on-line fractionation procedure to result in a better therapeutic ratio than conventional FT. The following discussion focuses on several strategies for on-line fractionation.

1. Theory 1.1 Assumptions

A radiation therapy treatment plan is to deliver a total dose of D to the tumor in N fractions. The configurations of relative OAR versus tumor positions may vary from fraction to fraction. Without losing generality, it is assumed that the OAR relative to tumor position has potential M configurations during the whole course of treatment. For the configuration m, let the ratio of OAR dose over the tumor dose be $r_m$ with $\{r_m\}$ sorted in increased order ($r_1 < r_2 < \ldots < r_M$). Here, "dose" is a generalized term; it can be any value based on the dose distribution, such as mean dose, minimum dose, maximum dose, dose of a representing point, dose of certain volume, equivalent uniform dose (EUD), biologically effective dose (BED), tumor control probability (TCP), and normal tissue complication probability (NTCP), etc. The configurations can be evaluated by moving the OAR location around a single planning dose distribution.

Figure 7:
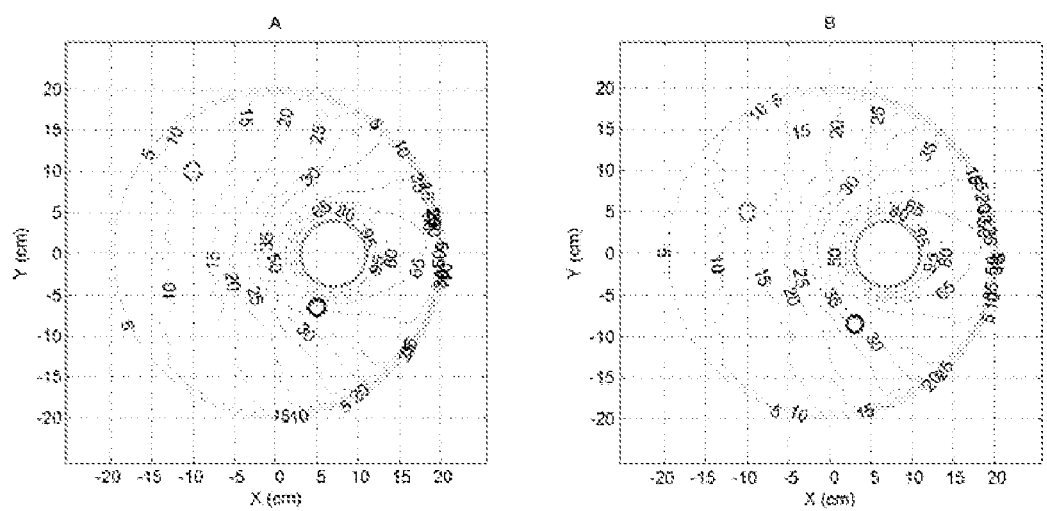
FIG. 7 illustrates a graphical evaluation of the configuration (OARDose/tumorDose) for each treatment fraction. Graphs A and B show two fractions. The isodose lines show the planned dose distributions. The positions of tumor and OARs are delineated from the daily images and overlapped with the planned dose distribution.

FIG. 7 illustrates how to evaluate the configuration for each fraction based on the planned dose distribution and daily image guidance. Here, the evaluation of the configuration is to determine the ratio of the mean OAR dose to the prescribed tumor dose. Assume that image-guided setup always puts the tumor in the planned position (e.g. 95% isodose line), but the positions of OARs vary from fraction to fraction. FIG. 7 illustrates two OARs with OAR1 (blue) in the high dose gradient region and OAR2 (pink) in the low dose gradient region. For OAR2, the position variation does not result in significant dose variation and therefore benefit little from adaptive fractionation. For OAR1, the position variations result in significant dose variation. Its configuration (mean OARDose/tumorDose) changes from 50% (graph A) to 30% (graph B). FIG. 7 also shows that only the planned dose distribution and relative position information of the tumor and OAR on each day of treatment is needed for AFT. In other words, for AFT, the system does not need to perform re-planning (re-optimization), dose calculation, or a volumetric image. To perform AFT, the system only needs the relative OAR position information, which can be acquired from portal images, 2D images, implanted seeds, etc.

Let $d_n$ be the fraction size for the nth fraction and $c_n \in [1, M]$ be its corresponding configuration, then the cumulative tumor dose for the whole course of treatment is:

$$D^{tumor} = \sum_{n=1}^{N} d_n \qquad (1)$$

and the cumulative OAR dose is:

$$D^{OAR} = \sum_{n=1}^{N} r_{c_n} d_n \qquad (2)$$

The objective of the fractionation procedure is to find the sequence $\{d_n\}$ that minimizes $D^{OAR}$ while maintaining the same tumor dose $D^{tumor}=D$. For all strategies to be discussed, besides the cumulative tumor dose constraint $$\sum_{n=1}^{N} d_n = D,$$

the following bound constraints are used: $\underline{d} \leq d_n \leq \overline{d}$, $\forall n$, where $$\underline{d} \leq \frac{D}{N} \text{ and } \overline{d} \geq \frac{D}{N}$$

are the lower bound and upper bound for the fraction size. These bound constraints serve to maintain the similar radiobiological effects as a conventional radiotherapy protocol.

In the following sections, two extreme strategies are introduced, and then the adaptive fractionation strategy is derived. These extreme strategies, namely regular fractionation and gold standard fractionation, provide bottom and top baselines to evaluate other fractionation techniques.

1.2 Regular Fractionation

The regular fractionation strategy is just the conventional radiotherapy protocol, that is, all fractions have the same size:

$$d^n = \frac{D}{N} \qquad (3)$$

The total OAR dose from regular fractionation is:

$$D^{OAR} = \frac{D}{N} \sum_{n=1}^{N} r_{c_n} \qquad (4)$$

Regular fractionation provides a bottom baseline for other strategies. Any adaptive fractionation technique should have smaller $D^{OAR}$ than the regular fractionation in order to be considered valuable.

1.3 Gold Standard Fractionation

Suppose the configurations for all N fractions $\{c_n\}$ $\{c_1, c_2, \ldots c_N\}$ is known before delivery. Then the best fractionation strategy $\{d^n\}$ is to solve the following linear programming (LP) problem:

$$\min_{\{d^n\}} \sum_{n=1}^{N} (r_{c_n} d_n) \qquad (5)$$

subject to:

$$\sum_{n=1}^{N} d_n = D \qquad (6)$$

$$\underline{d} \leq d_n \leq \overline{d}, (\forall n \in [1, N]) \qquad (7)$$

It should be noted that in practice, it is very unlikely that all the configurations $\{c_n\}$ $\{c_1, c_2, \ldots c_N\}$ are known before delivery of treatment. Therefore, this strategy only exists in retrospective studies. Consequently, it is used as a top baseline for evaluating other fractionation techniques.

1.4 Varied Fractionation

Because different fractions may have different anatomical configurations, either favoring or disfavoring OAR sparing, a simple fractionation strategy is to use the same fraction size for the same configuration. That is:

$$d_n = t_m \text{ (if } c_n = m) \qquad (8)$$

The following discusses the strategy to determine $\{t_m\}$

Though generally we do not know the configuration sequence $\{c_n\}$ before delivery, often there is some a priori knowledge available about its probability distribution $\{p_m\}$. Then, if the number of fractions N is sufficiently large, the expected cumulative tumor dose is:

$$\langle D^{target} \rangle = \sum_{m=1}^{M} t_m (N p_m) = N \sum_{m=1}^{M} r_m p_m \qquad (9)$$

and the expected cumulative OAR dose is:

$$\langle D^{OAR} \rangle = \sum_{m=1}^{M} r_m t_m (N p_m) = N \sum_{m=1}^{M} r_m t_m p_m \qquad (10)$$

Then, in order to determine $\{t_m\}$, a solution to the following problem is required:

$$\min_{\{t_m\}} \sum_{m=1}^{M} p_m r_m t_m \qquad (11)$$

subject to:

$$\underline{d} \leq t_m \leq \overline{d} \qquad (12)$$

and $$N \sum_{m=1}^{M} p_m t_m = D \qquad (13)$$

The problem with this simple strategy is that it may not be able to deliver the total dose D in exactly N fractions with both lower bound $\underline{d}$ and upper bound $\overline{d}$ being met.

1.5 Adaptive Fractionation

It should be noted that in optimization of simple varied fractionation as given in Eqs. (11)-(13), no information about previous delivered dose and/or the current fraction configuration $c_n$ are used. Such a simple strategy may result in a nonfeasible delivery sequence. For adaptive fractionation, to obtain a feasible and "optimal" delivery sequence $\{d_n\}$, it is necessary to modify simple fractionation Eqs. (11)-(13) to include such information.

Let the remaining dose before the nth fraction delivery be:

$$R_n = D - \sum_{1}^{n-1} d^k \quad (14)$$

Suppose there is prior knowledge of the probability distribution of configurations for all remaining (k>n) fractions $\{p_m\}$. To determine the current fraction size $d_n$, the following strategy is used:

If n=N, then $d_N=R_N$,
else, we solve following LP problem:

$$\min_{d_n, \{t_m\}} \left( r_{c_n} d_n + (N-n) \sum_{m=1}^{M} p_m r_m t_m \right), (n < N) \quad (15)$$

subject to:

$$\underline{d}_n \leq d_n \leq \overline{d}_n \quad (16)$$

$$\underline{d} \leq t_m \leq \overline{d} \quad (17)$$

and $$d_n + (N-n) \sum_{m=1}^{M} p_m t_m = R_n \quad (16)$$

where:

$$\underline{d}_n = \max(\underline{d}, R_n - (N-n)\overline{d}) \quad (19)$$

$$\overline{d}_n = \min(\overline{d}, R_n - (N-n)\underline{d}) \quad (20)$$

Note that Eq. (15) serves to minimize the expected OAR dose for the remaining fractions. Eq. (18) is the cumulative tumor dose constraint. Eq. (16) and Eq. (17) place constraints on the fraction size so that all fractions meet the lower and upper bounds. It can be verified that this strategy will deliver the total dose D in exactly N fractions with both lower bound and upper bound of fraction size met for all fractions.

2. Simulations

Simulations can be used to verify and validate the proposed adaptive fractionation strategy. The fractionation strategies and simulations are implemented using Matlab programming language. The LP problems are solved using the LP solver in optimization toolbox associated with Matlab.

In the simulations, it is assumed that there are M=100 configurations, with the ratio of OAR to tumor dose $r_m$=m/M for configuration m. The following normalized Gaussian distribution is defined as the probability density function (PDF) of the configurations:

$$p_{\sigma,\mu}(m) = \frac{\exp[-(r_m - \mu)^2/\sigma^2]}{\sum_{m=1}^{M} \exp[-(r_m - \mu)^2/\sigma^2]} \quad (21)$$

where $\sigma$ is approximately the standard deviation and $\mu$ is approximately the mean of PDF. By changing $\sigma$ and $\mu$, we get different distributions.

2.1 Treatment Course Simulations

Figure 8:
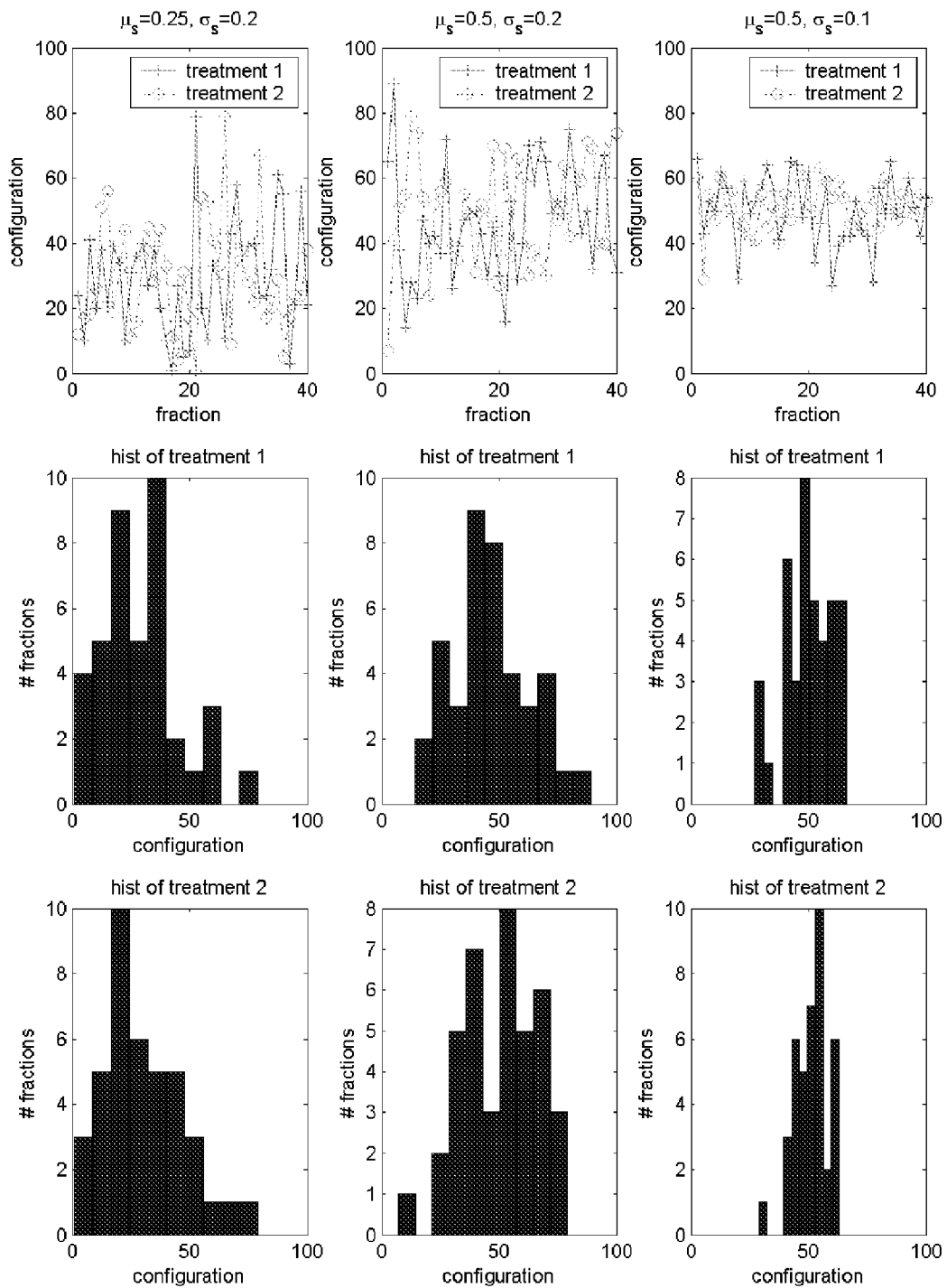
FIG. 8 illustrates examples of treatment course simulations.

A distribution $p^{sim}=p_{\sigma_s,\mu_s}$ is used to simulate the configuration sequence for a treatment course. That is, for a certain treatment course, a configuration sequence $\{r_n\}$, (n=1, 2, N) for each fraction is simulated, where $r_n$ is sampled using a Monte Carlo method with the PDF given by $p^{sim}=p_{\sigma_s,\mu_s}$. For all simulations, it is assumed that the treatment course consists of N=40 fractions and the prescribed tumor dose is 80 Gy. FIG. 8 shows two examples of the simulated treatment courses for each combination of $\{\sigma_s, \mu_s\}$. For each set of $\{\sigma_s, \mu_s\}$, 1000 treatment courses are simulated and tested to approach a good statistic.

2.2 Fractionation Strategies

For each treatment course, the regular fractionation, the gold standard fractionation, and the adaptive fractionation as discussed above are used to determine the delivery schemes. Note that in the adaptive fractionation formula, a PDF of configurations for the remaining fractions is needed to optimize the current fraction size. This PDF is regarded as a model of a priori knowledge, which may or may not reflect the realities. In these simulations, to study the efficiency as well as the robustness of the adaptive fractionation strategy, the following two different models were used: (1) the "fine" model and (2) the "coarse" model. The "fine" model should be used if there is accurate information about the future distributions. The same PDF for the treatment course simulation is used as the fine model:

$$p^{adaptive}_{fine}(m) = p^{sim}(m), \forall m \quad (22)$$

The "coarse" model should be used if there is very little information about the probability distributions of the future fractions. A simple flat PDF for any treatment course is used as the coarse model:

$$p^{adaptive}_{coarse}(m) = \frac{1}{M}, \forall m \quad (23)$$

2.3 Bounds on Fraction Size

Due to the uncertainty and biological effects of radiation therapy, an arbitrary large or small dose cannot be delivered in any fraction. The conventional 2 Gy/fraction is used as the nominal fraction size. Two different bounds, the tight bound with $\underline{d}=1$ Gy and $\overline{d}=3$ Gy, and the loose bound with $\underline{d}=0$ Gy and $\overline{d}=4$ Gy are tested in these simulations to mimic clinical requirements.

3. Evaluations

For a certain simulated treatment course $\{r_n\}$ and each fractionation strategy, a delivery sequence $\{d_n\}$ is obtained. Cumulative tumor dose $D^{tumor}$ and cumulative OAR dose $D^{OAR}$ are then calculated according to Eq. (1) and (2) respectively. The cumulative tumor doses are verified to be the same as the prescribed dose D. The cumulative OAR doses are used as a metric to evaluate the efficiency of the fractionation strategy. The histograms and other statistics of the cumulative OAR dose are calculated and compared.

The "absolute gain" from certain fractionation strategy F for a simulated treatment course k is defined as:

$$G_F(k) = D^{OAR}_{F0}(k) - D^{OAR}_F(k) \quad (24)$$

where F0 stands for regular fractionation. Here the gain is a simple metric for OAR sparing—the larger the gain, the better the OAR sparing.

The relative gain $g_F(k)$ for treatment course k is defined as:

$$g_F(k) = \frac{G_F(k)}{D_{F0}^{OAR}(k)} \quad (25)$$

The mean absolute gain $\overline{G}_F$ and mean relative gain $\overline{g}_F$ are calculated as the mean over K=1000 simulated courses:

$$\overline{G}_F = \frac{1}{K}\sum_{k=1}^{K} G_F(k) \quad (26)$$

$$\overline{g}_F = \frac{1}{K}\sum_{k=1}^{K} \frac{G_F(k)}{D_{F0}^{OAR}(k)} \quad (27)$$

4. Results

For all simulated treatment courses and associated delivery sequence $\{d_n\}$ from three different fractionation strategies (regular, gold standard and adaptive), it has been verified that $\underline{d} \leq d_n \leq \overline{d}$, $\forall n$ and $$\sum_{1}^{N} d_n = D,$$

which means that all strategies generate feasible delivery sequences for all test cases.

Figure 9:
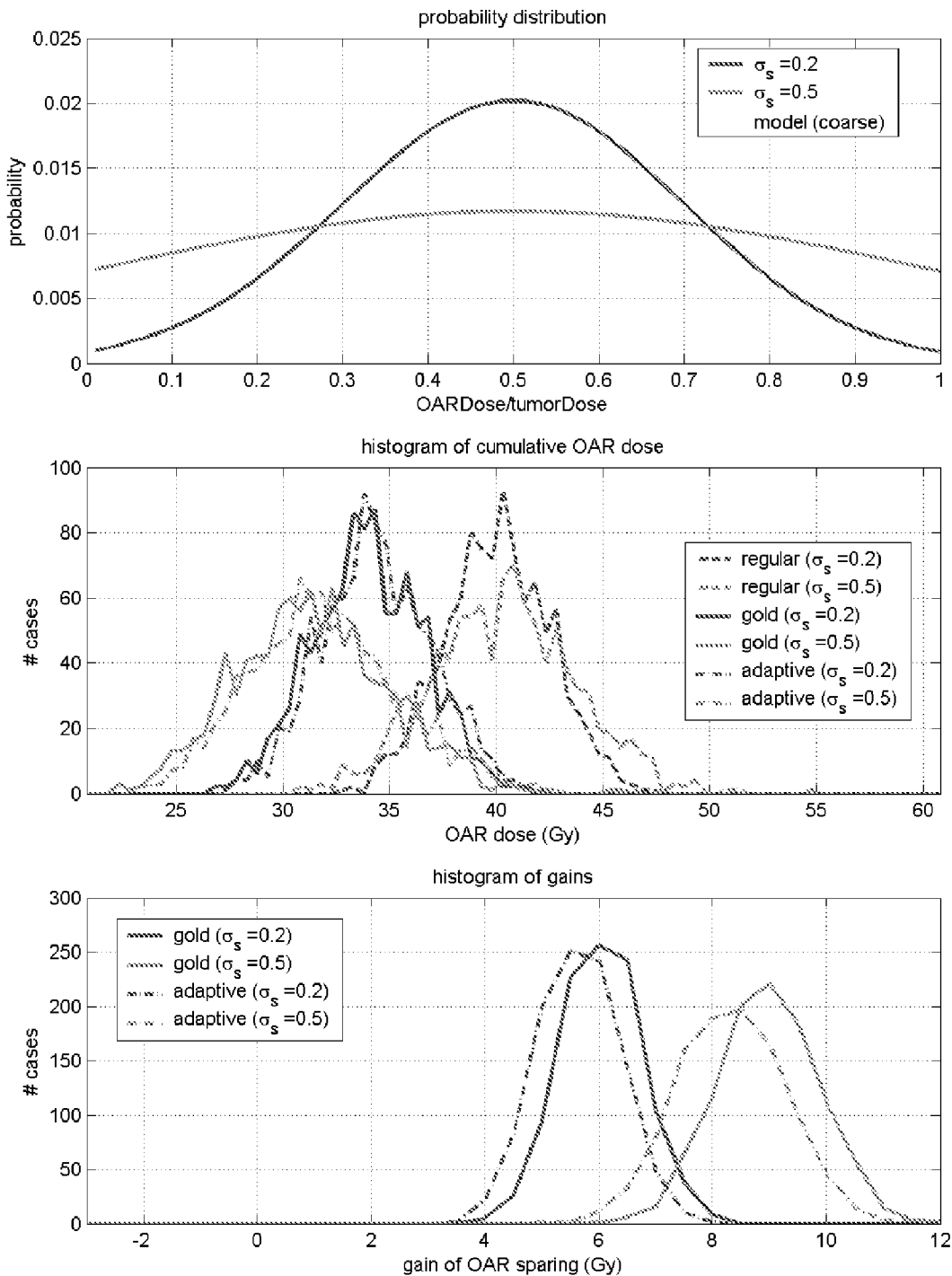
FIG. 9 graphically illustrates the efficiencies of different fractionation strategies vs. configuration variations.

FIG. 9 illustrates the efficiencies of different fractionation strategies vs. configuration variations. The efficiencies are indicated by the cumulative OAR doses over 40 fractions and the gains of OAR sparing are compared with the regular fractionation. The configuration variations are defined as standard distribution $\sigma_s$ used in the treatment courses simulations. FIG. 9 compares results from two different configuration variations, $\sigma_s$=0.2 and $\sigma_s$=0.5. The bounds used in the gold standard fractionation and the adaptive fractionation strategies are $\underline{d}$=1 Gy and $\overline{d}$=3 Gy. Fine model PDF is used in the adaptive fractionation strategy.

The top graph of FIG. 9 shows the PDFs for Monte Carlo simulations of treatment courses. The middle graph shows the histograms of cumulative OAR dose over 40 fractions of 1000 treatment courses. It is evident that for both configuration variation schemes, the regular fractionations have histograms of cumulative OAR doses centered around 40 Gy, which is consistent with the simulation of treatment courses with $\mu$=0.5 and D=80 Gy. The spreads of histograms are due to the finite number of fractions per treatment course (N=40). Compared to the regular fractionations, the gold standard fractionations have the histograms shifted to the left. The larger the configuration variations, the more the shift, which means that the gold standard fractionation results in smaller cumulative OAR dose than the regular fractionation. The histograms from adaptive fractionations are similar to those from the gold standard fractionations, which indicates that the adaptive fractionation strategies work pretty well if the a priori knowledge model accurately describes the reality. The bottom graph of FIG. 9 shows the histograms of the absolute gains of OAR sparing results from the gold standard and the adaptive fractionation schemes for 1000 treatment course simulations. The absolute gains of OAR sparing for regular fractionations are defined as zero. It is evident that the gold standard fractionations have slightly better OAR sparing than the adaptive fractionations for the same configuration variations, which is expected because the gold standard fractionations use retrospective strategies while the adaptive fractionations use perspective strategies. The OAR sparing from adaptive fractionation is positive for all simulated treatment courses. The minimal gain is above 3 Gy while the maximal gain is about 12 Gy. This indicates that the adaptive fractionation scheme presented above is capable of achieving better OAR sparing if the variations of configurations are significant and identifiable.

Figure 10:
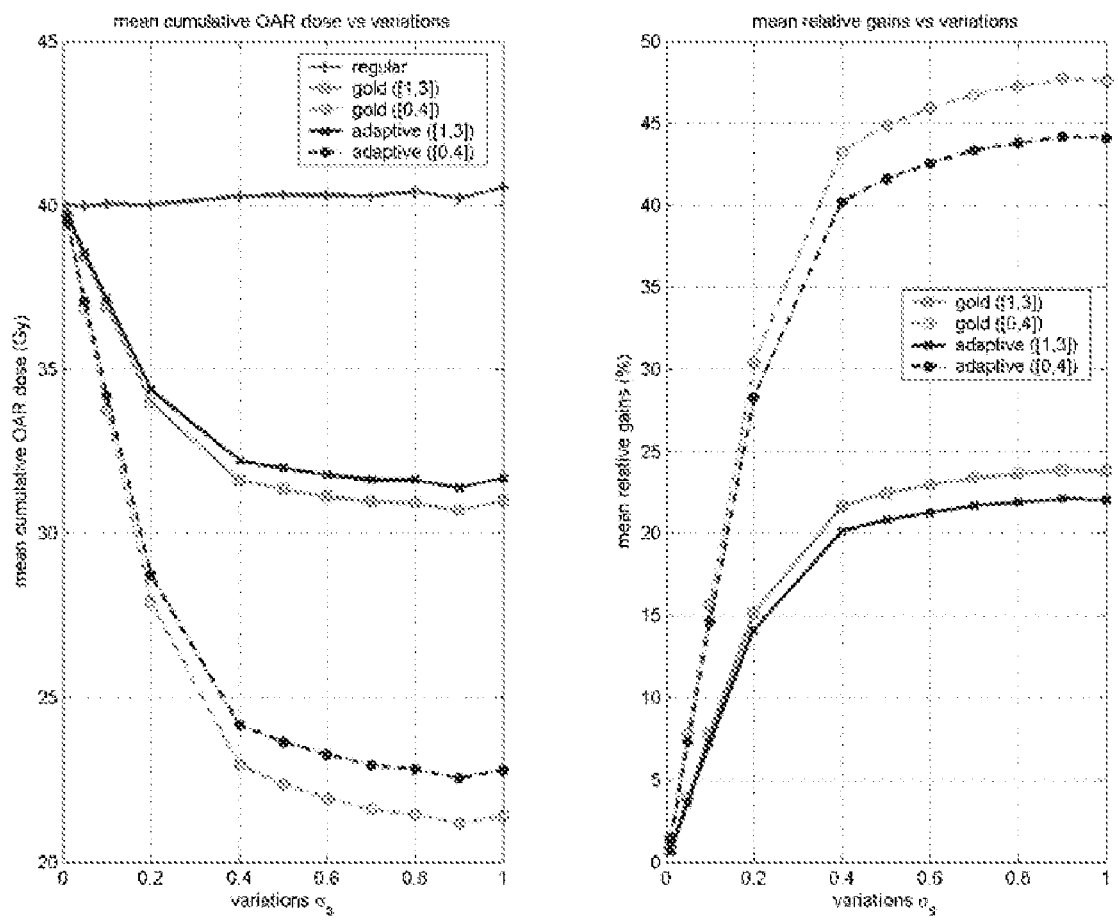
FIG. 10 graphically illustrates comparisons of the mean cumulative OAR doses and mean relative gains from different fractionation strategies vs. the configuration variations.

FIG. 10 illustrates the efficiencies of different fractionation strategies vs. configuration variations and the bounds of fraction sizes. The left graph shows the mean cumulative OAR dose vs. variations. The right graph shows the mean relative gains vs. configuration variations. Here, the means are calculated over 1000 simulated treatment courses. Two different bounds of fraction sizes, the tight bound ($\underline{d}$=1 Gy, $\overline{d}$=3 Gy), and the loose bound ($\underline{d}$=0 and $\overline{d}$=4 Gy) are compared. This illustrates that the gold standard and adaptive fractionation schemes with the loose bound result in lower OAR doses than with the tight bound, which is consistent with the intuitive expectation. The loose bound means larger flexibility to choose fraction size and usually results in a better strategy. If the bound is as tight as $\underline{d}$=$\overline{d}$=2 Gy, then to deliver 80 Gy in 40 fractions, it is necessary to deliver 2 Gy in every fraction for any strategy used, which is the same as regular fractionation, and there is no gain at all. It also illustrates that the larger the variations, the greater the gains. As for the tight bound used, the mean relative gains of OAR sparing are around 7.5% for $\sigma_s$=0.1, 15% for $\sigma_s$=0.2, 20% for $\sigma_s$=0.4, 22% for $\sigma_s$=0.8. The gains are higher for the loose bound used, but with the same trends. This is also consistent with the intuitive expectation—"no variation, no choice." If all the fractions have the same configurations, then no matter what fractionation scheme is used, the total OAR dose will be the same because there are constraints that the total tumor dose be the same.

Figure 11:
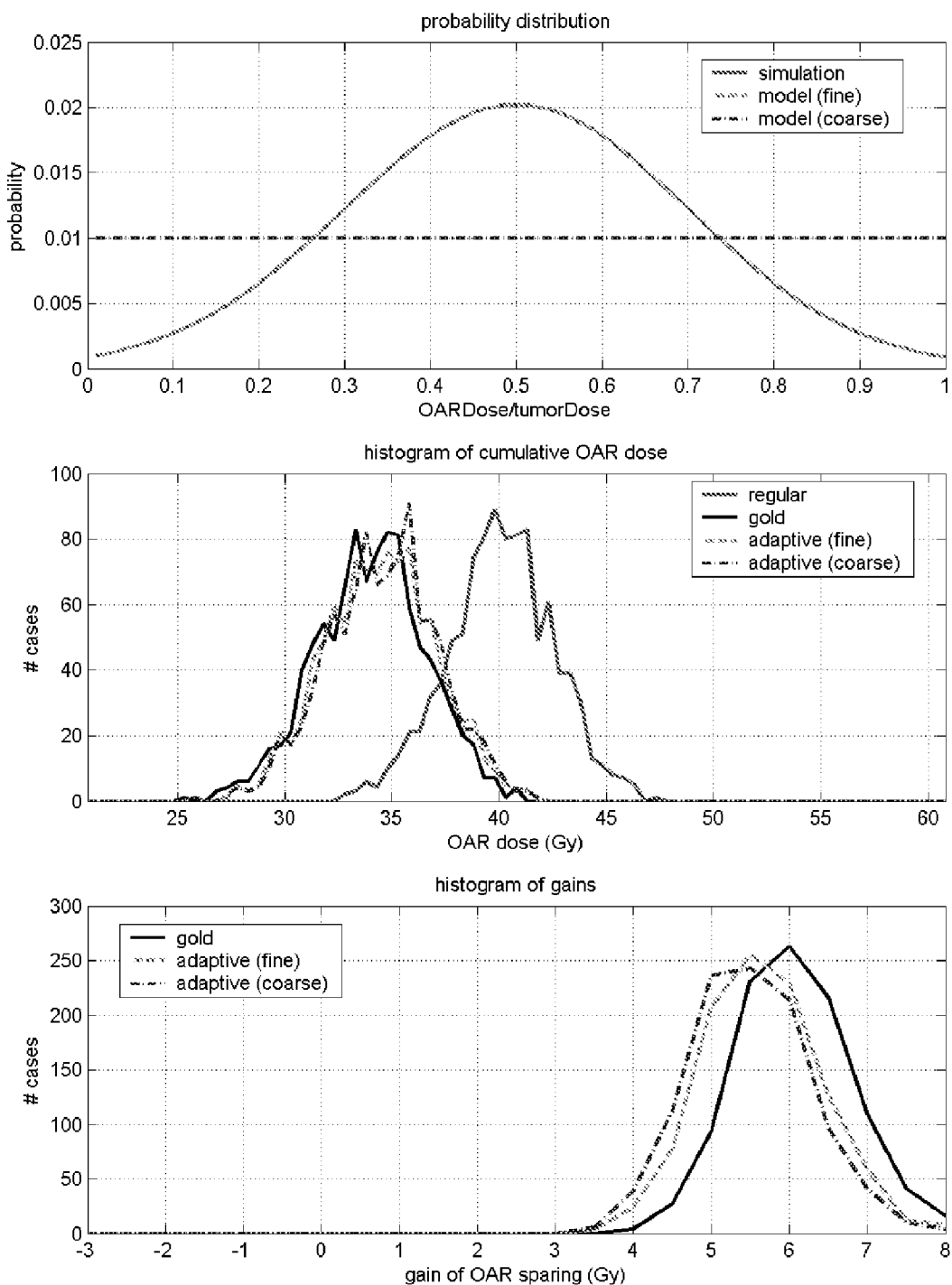
FIG. 11 graphically illustrates comparisons of adaptive fractionation versus regular and gold standard fractionations.
Figure 12:
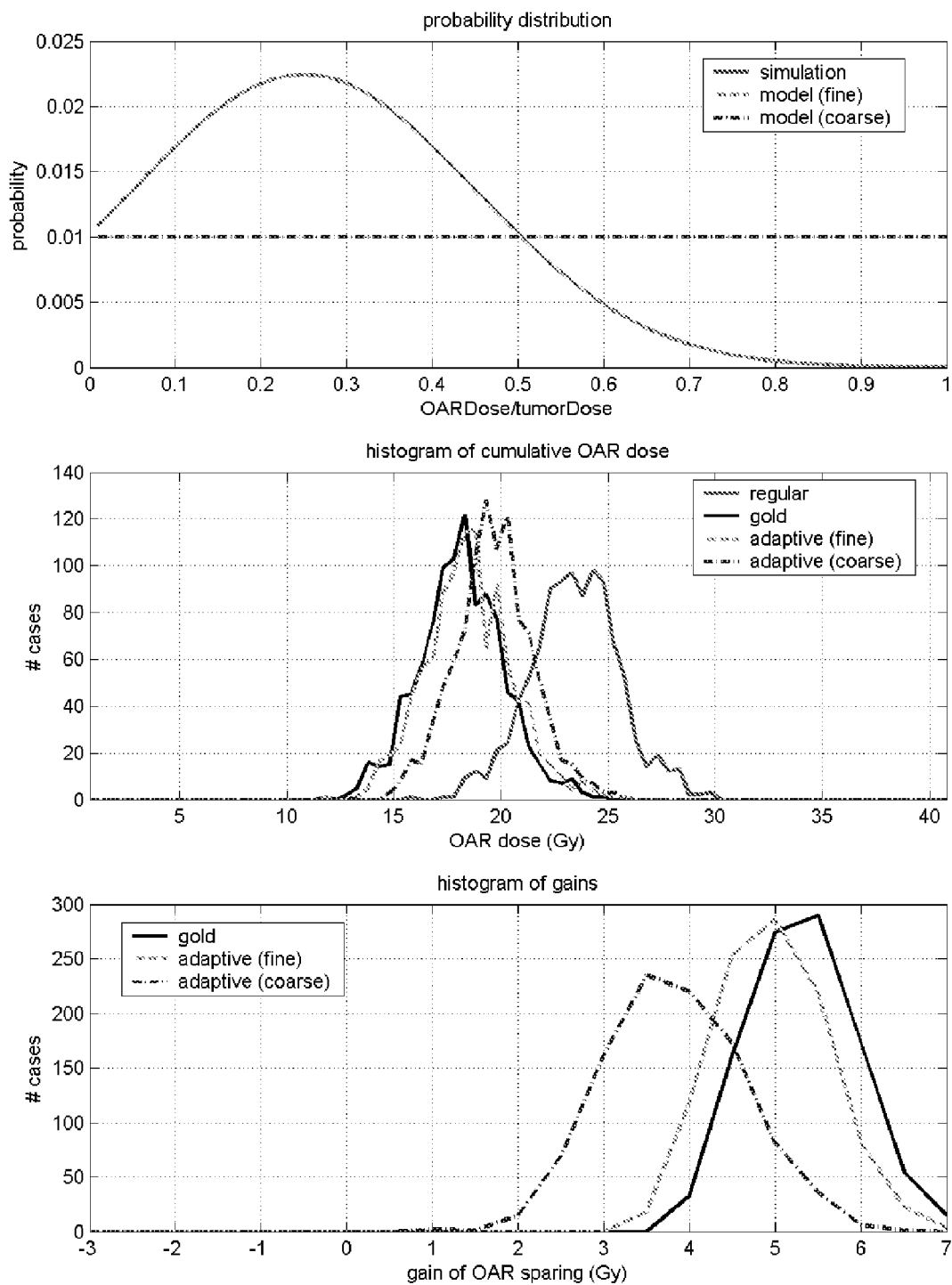
FIG. 12 graphically illustrates comparisons of adaptive fractionation vs. regular and gold standard fractionations (as in FIG. 11) except that a different PDF for treatment course simulation and model one of adaptive fractionation is used.
Figure 13:
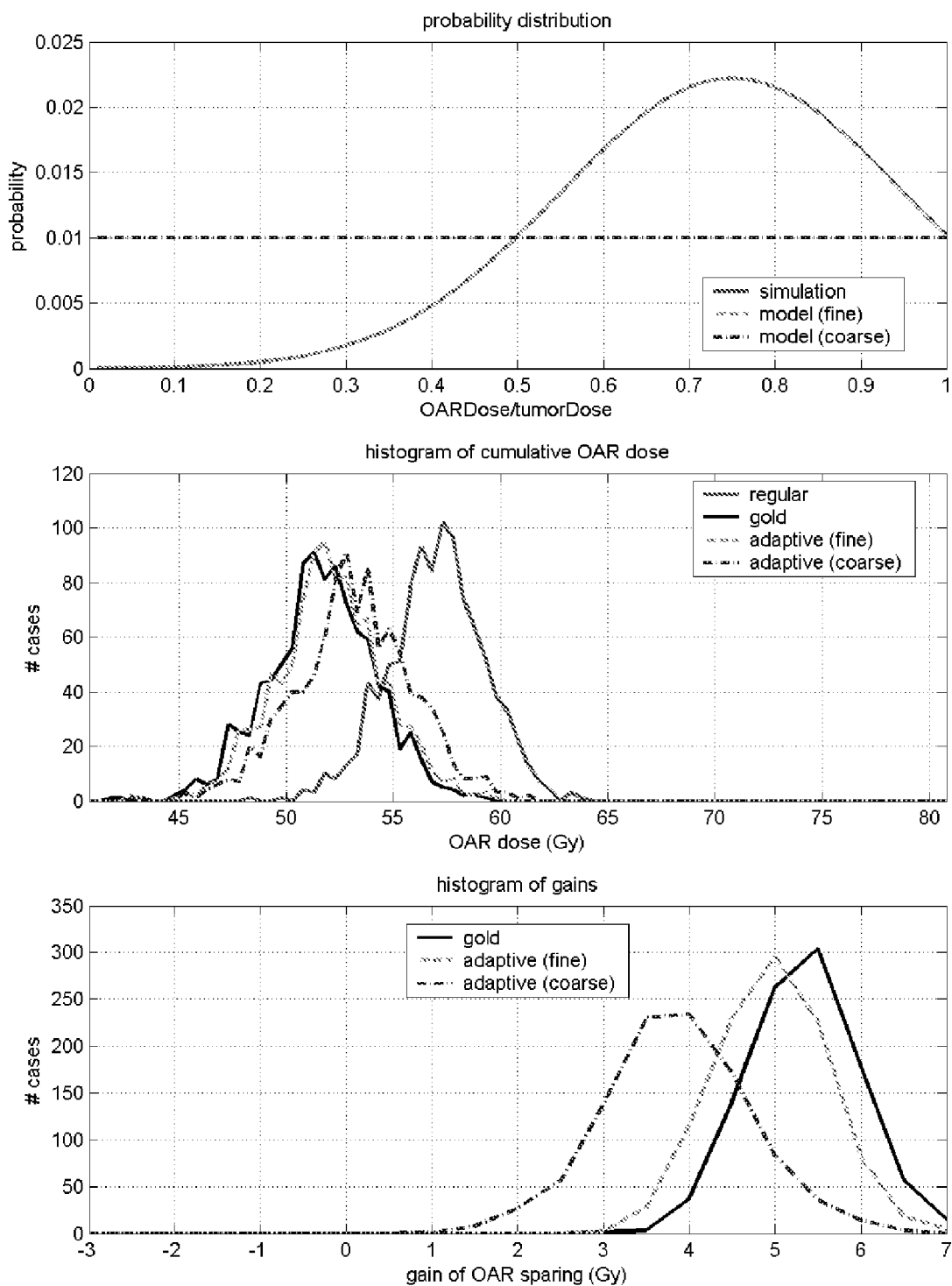
FIG. 13 graphically illustrates comparisons of adaptive fractionation vs. regular and gold standard fractionations (as in FIG. 11) except that a different PDF for treatment course simulation and model one of adaptive fractionation is used.

FIGS. 11-13 illustrate how different a priori knowledge models affect the results of adaptive fractionations. Both fine and coarse PDF models are compared. The fine model uses the same PDF as the treatment courses simulation. The coarse model uses a simple flat PDF. All treatment courses are simulated using $\sigma_s$=0.2 but with different $\mu_s$. FIG. 11 has $\mu_s$=0.5, which indicates that the OAR at nominal position will receive 50% of tumor dose. FIG. 12 has $\mu_s$=0.25, which indicates that the OAR will receive about 25% of tumor dose at nominal position, simulating the situation in which the OAR is away from the tumor. FIG. 13 has $\mu_s$=0.75, which indicates that the OAR will receive about 75% of the tumor dose at nominal position, simulating the situation in which the OAR is close to the tumor. The top graphs show the PDF used in simulations and in the adaptive fractionation strategy. The middle graphs show the histograms of the cumulative OAR dose from 1000 treatment course simulations. The bottom graphs show the histograms of absolute gains of OAR sparing from 1000 treatment course simulations. Table 1 summarizes the mean cumulative doses and mean relative gains of OAR sparing for different fractionation strategies. As for the fine model used in adaptive fractionation strategy, all three figures show that the adaptive fractionations closely approach the gold standard. The mean, minimal, and maximal gains of the gold standard fractionation are only about 0.5 Gy higher than the adaptive fractionation. The mean absolute gains of OAR sparing of adaptive fractionations are 5.0 Gy, 5.7 Gy, and 5.0 Gy for $\mu_s$=0.25, 0.5 and 0.75 respectively. The minimal gains are 3 Gy and the maximal gains are around 7-8 Gy for all three simulated cases. The mean gains of OAR sparing for the adaptive fractionations using the coarse model are 3.9 Gy, 5.5

Gy, and 3.9 Gy for $\mu_s$=0.25, 0.5, and 0.75 respectively, which are about 1.1 Gy, 0.2 Gy, and 1.1 Gy worse than the adaptive fractionations using the fine model. The minimal gains of OAR sparing for the adaptive fractionations using the coarse model are 0.9 Gy, 2.7 Gy, and 1.0 Gy for $\mu_s$=0.25, 0.5, and 0.75 respectively. The mean relative gains of OAR sparing for the adaptive fractionations using the fine model are 21.2%, 14.1%, and 8.7% for $\mu_s$=0.25, 0.5, and 0.75 respectively, these numbers decreased to 16.3%, 13.8%, and 6.8% for the coarse model used in adaptive fractionation.

TABLE 1

| | Mean cumulative OAR dose in Gy (mean relative gain) | | | |
|---|---|---|---|---|
| Simulations | regular | gold standard | Adaptive (fine) | Adaptive (coarse) |
| $\mu_s$ = 0.25 | 23.5 | 18.1 (%22.8) | 18.5 (%21.2) | 19.6 (%16.3) |
| $\mu_s$ = 0.5 | 40.1 | 34.0 (%15.2) | 34.4 (%14.1) | 34.6 (%13.8) |
| $\mu_s$ = 0.75 | 57.0 | 51.7 (%9.4) | 52.0 (%8.7) | 53.1 (%6.8) |

5. Discussion

Adaptive radiation therapy (ART) generally refers to the concept of using feedback before and/or during the course of radiation therapy treatment to improve future treatment. Feedback can be used in off-line adaptive processes or on-line adaptive processes. Off-line ART processes occur while the patient is not being treated, such as in between treatment fractions. Images and dose data from the previous fractions are collected and evaluated. A new treatment plan is developed to better reflect the range of motion of the target and/or corrections of previous delivery errors from all kinds of sources, such as setup errors, organ deformations, etc. Off-line adaptive processes are usually time-consuming because they involve the re-optimization of a new treatment plan, generation of a new deliverable fluence map and the commissioning of that plan. On-line adaptive processes occur when the patient is in the treatment room (e.g., substantially in a treatment position) and potentially, right before or during the treatment delivery. The AFT discussed above is an on-line adaptive process. The on-line data, such as CT images, may not be used to optimize a new treatment plan, but rather to optimize a fraction size that provides the best overall OAR sparing. The technique utilizes the fraction to fraction variations of internal structures to obtain maximal gains. It is appealing because it does not require much extra human interaction except to identify the configuration. The problem size for on-line optimization is so small (number of fractions× number of configurations) that the on-line fractionation takes virtually no extra time. The gains are significant.

Though cumulative OAR dose is only used as the objective, and cumulative tumor dose and bounds on fraction size as constraints to derive the adaptive fractionation scheme, other radiobiological models, such as BED, TCP/NTCP, etc., can be incorporated into the adaptive fractionation optimization. In those cases, a general non-linear programming optimization may be involved as well. The total number of fractions and/or total tumor may change as the treatment and adaptive fractionation scheme progresses.

6. Conclusions

Adaptive fractionation therapy is an on-line adaptive technique that utilizes the variations of internal structures, especially the variations of tumor-OAR distance, to derive an optimal fractionation scheme with the largest gains of the therapeutic ratio. Changes of internal structures are classified as different configurations according to their feasibility to the radiation delivery. A priori knowledge is used to describe the probability distribution of these different configurations. On line processes include identifying the configuration and optimizing the current fraction size. A simple linear programming problem is used as the optimization tool.

Extensive simulations which include thousands of treatment courses with each course consisting of 40 fractions have been used to test the efficiency and robustness of the presented technique. The gains of OAR sparing depend on the variation of configuration and the bounds on the fraction size. The larger the variation and the looser the bounds, the larger the gains. For a typical 20% tumor-OAR configuration variation and [1 Gy, 3 Gy] bounds, the gains of OAR sparing are around 5-6 Gy, or 9-18%, for a fine a priori model and a prescribed dose of 80 Gy in 40 fractions. Even when a coarse a priori model is used, the gains are still as large as 4-5 Gy, or 7-16%, as compared to the conventional fractionation technique.

II. Introduction to Adaptive Fractionation Based on Biological Optimization

In the previous section, the adaptation is based on the regularly defined dose without biological formulation—the objective is to minimize the OAR dose and the constraint is to maintain the tumor dose. In this section, the adaptation strategy based on the linear-quadratic cell survival model is examined. It is assumed that there are finitely many OAR/tumor dose ratios and the probability of their occurrence is known. However, unlike the previous optimization approach, a fraction size lookup table is built from bottom up for each fraction. The fraction size for the current fraction is determined by maximizing the future expected survival of the OAR and preserving the tumor cell kill. Extensive simulations demonstrate the effectiveness of this method compared with the conventional fractionation method.

Radiation therapy can be fractionized to increase the normal tissue sparing and maintain the same level of tumor cell kill simultaneously in terms of surviving fractions when both surviving fractions are described using the linear quadratic model and the α/β ratio of the tumor is higher than that of the sensitive structures (i.e., OAR). The conventional approach is to use an equal fraction size for each fraction. However, that does not take into account the variations of the OAR/tumor dose ratio. The OAR/tumor dose ratio changes when the relative position of OAR and the tumor changes, which can happen along a treatment course. Intuitively, this variation can be taken advantage of by delivering more doses when the ratio is lower and fewer doses when the ratio is higher. However, the question of exactly how much dose should be delivered remains to be answered. In the previous section, the concept of adaptive fractionation is explained and a strategy is presented. Nevertheless, the adaptation in that section is based on the regularly defined dose; that is, the objective function and constraint are the dose received by OAR and the tumor, respectively.

To account for the biological effect, the regularly defined dose is modified to biologically effective dose (BED). The method presented in the previous section can no longer apply when considering BED. In this section, instead, the objective function and constraint are the biologically effective dose (BED) for OAR and the tumor, respectively. BED is a quantity derived from the surviving fraction. We assume the OAR/tumor dose ratios satisfy a normal distribution. Inductively then, an expected BED of OAR can be defined with the constraint being the BED of the tumor. In each inductive step, the fraction size is constructed as a function of dose ratio and the remaining tumor BED. This inductively built fraction size lookup table can then be used for on-line determination. Simulations demonstrate the effectiveness of this method compared with the equal fraction size method.

The following is a list of notations that are used throughout this section:

N, the number of fractions $d_i$, dose (fraction size) for the i-th fraction $r_i$, OAR/tumor dose ratio for the i-th fraction $\alpha_R$, the constant of the linear term for the OAR survival curve $\beta_R$, the constant of the quadratic term for the OAR survival curve $(\alpha/\beta)_R$, the $\alpha\beta$ ratio for the OAR survival curve $\alpha_T$, the constant of the linear term for the tumor kill $\beta_T$, the constant of the quadratic term for the tumor kill $(\alpha/\beta)_T$, the $\alpha\beta$ ratio for the tumor 1. Method In this section, first the model of BED is reviewed. Then, the adaptive fractionation is formulated in a constrained optimization problem when the dose ratios of all fractions are available. In real situations, the dose ratios are only available up to the current fraction. Therefore, the optimization problem is modified in terms of expectation. The basic assumption is that the probability distribution of the OAR/tumor dose ratio is known. The problem is then solved by building up inductively a fraction size lookup table. The pseudo code for generating such a table is also presented.

The linear-quadratic model for the surviving fraction is $$S_T = \exp(-(\alpha_T d + \beta_T d^2)) \quad (28)$$

and $$S_R = \exp(-(\alpha_R d + \beta_R d^2)) \quad (29)$$

for the tumor and OAR, respectively, if they receive dose d. The biologically equivalent dose (BED) according to the above surviving fraction model is $$BED = d + \frac{d^2}{\alpha/\beta} \quad (30)$$

If the fraction sizes are $\{d_1, \ldots, d_N\}$, then the resulting tumor survival is $$S_T = \exp\left(-\sum_{i=1}^{N}(\alpha_T d_i + \beta_T d_i^2)\right) \quad (31)$$

Suppose the dose ratios $\{r_1, \ldots, r_N\}$ are known, the adaptive fractionation problem is to determine $\{d_1, \ldots, d_N\}$ so that the tumor survival in Eq. (31) is a constant while the OAR survival is maximized.

$$S_R = \exp\left(-\sum_{i=1}^{N}(\alpha_R d_i r_i + \beta_R (d_i r_i)^2)\right) \quad (32)$$

In terms of BED, the problem can be formulated as $$\min_{\{d_1,\ldots,d_N\}} \sum_{i=1}^{N} d_i r_i + \frac{(d_i r_i)^2}{(\alpha/\beta)_R} \quad (33)$$

$$\text{subject to } \sum_{i=1}^{N} d_i + \frac{d_i^2}{(\alpha/\beta)_T} = C$$

where C is a constant. The objective function is the BED of OAR and the constraint is the BED of the tumor. The formulation in Eq. (33) can be established if the dose ratios of all fractions are known. In reality, the future dose ratios are not available. Therefore, the formulation of Eq. (33) needs to be modified using expectations. The strategy is to determine the fraction size inductively from the single fraction case.

Suppose there is only one fraction. Then the equation $$d_1 + \frac{d_1^2}{(\alpha/\beta)_T} = C \quad (34)$$

completely determines $d_1$. In fact, $d_1$ can be written as a function of C.

$$d_1 = h(C) = \frac{1}{2}\left(-(\alpha/\beta)_T + \sqrt{(\alpha/\beta)_T^2 + 4(\alpha/\beta)_T C}\right) \quad (35)$$

And the minimal OAR BED is $$d_1 r_1 + \frac{(d_1 r_1)^2}{(\alpha/\beta)_R} = r_1 h(C) + \frac{(r_1 h(C))^2}{(\alpha/\beta)_R} \quad (36)$$

regardless of what $r_1$ is. Its expected value is also a function of C.

$$f_1(C) = \langle r_1 \rangle h(C) + \frac{\langle r_1^2 \rangle h(C)^2}{(\alpha/\beta)_R} \quad (37)$$

$f_1(C)$ is the expected minimal OAR BED for any given tumor BED C when there is only one fraction. If there are two fractions and the tumor BED for the first fraction is $C_1$, then the tumor BED for the second fraction is $C-C_1$. From the viewpoint of the first fraction, the following equation should be minimized:

$$\min_{C_1} r_1 h(C_1) + \frac{r_1^2 h(C_1)^2}{(\alpha/\beta)_R} + f_1(C - C_1) \quad (38)$$

Then, for each possible value of $r_1$, there is a corresponding $C_1$ that minimizes Eq. (38). That is, $C_1$ is a function of $r_1$ and C. It follows that the minimum in Eq. (38) is also a function of $r_1$ and C. Let $g(r_1, C)$ denote the minimum in Eq. (38). In addition, the fraction size can be determined by $d=h(C_1)$. Therefore, the fraction size is also a function of $r_1$ and C. The expected minimal OAR BED is denoted by $f_2(C)$.

$$f_2(C) = \int g(r_1, C) p(r_1) dr_1 \quad (39)$$

This process can continue. In general, when there are n fractions and the total tumor BED is C, the objective function is $$\min_{C_1} r_1 h(C_1) + \frac{r_1^2 h(C_1)^2}{(\alpha/\beta)_R} + f_{n-1}(C - C_1) \quad (40)$$

There is no analytic form of $f_i$'s, but the optimization can still be solved numerically. As already mentioned, the solution $C_1$ uniquely determines the fraction sized. Therefore, we have inductively determined the fraction size d as a function of r, C and n.

2. Implementation

The formula for Eq. (40) defines a recursive rule from top down. That is, to determine the fraction size for the current fraction n, one needs to calculate $f_{n-1}$, hence $f_{n-2}, \ldots, f_1$. However, that calculation has exponential growth and is unapproachable. An alternative is to build a lookup table from bottom up and use linear interpolation when necessary. The lookup table of fraction sizes is a function of the remaining tumor BED, dose ratios and the remaining number of fractions. Note that the range of the remaining tumor BED varies for different fractions. Define $$C_{min} = d_{min} + \frac{d_{min}^2}{(\alpha/\beta)_T} \text{ and } C_{max} = d_{max} + \frac{d_{max}^2}{(\alpha/\beta)_T} \quad (41)$$

The total tumor BED $C_{Total}$ is calculated using d=2.

$$C_{Total} = N \cdot \left(2 + \frac{2}{(\alpha/\beta)_T}\right) \quad (42)$$

Then, when the number of remaining fractions is n, the range of tumor BED C is $$n \cdot C_{min} \leq C \leq \min(C_{Total}, n \cdot C_{max}) \quad (43)$$

A fixed sample size of 100 is used for all n, being cautious not to let the computation grow exponentially as the number of fractions increases.

The following is the pseudo code for generating the fraction size lookup table:

---

Fraction Size Lookup Table D(n, r, C)
n, the number of remaining fractions
r, the dose ratio
C, the tumor BED
Define D(1, r, C) = h(C) as in Eq. (35).

Define $g_1(r, C)$ using Eq. (36). $g_1(r, C) = rh(C) + \frac{(rh(C))^2}{(\alpha/\beta)_R}$.

Define $f_1(C)$ to be the expectation of $g_1(r, C) \cdot f_1(C) = \int g_1(r, C) p(r) dr$
For n = 2: N Define $D(n, r, C) = \arg\min_{C_1}\left(rh(C_1) + \frac{r^2 h(C_1)^2}{(\alpha/\beta)_R} + f_{n-1}(C - C_1)\right)$ Define $g_n(r, C) = \min_{C_1}\left(rh(C_1) + \frac{r^2 h(C_1)^2}{(\alpha/\beta)_R} + f_{n-1}(C - C_1)\right)$ Define $f_n(C)$ to be the expectation of $g_n(r, C) \cdot f_n(C) = \int g_n(r, C) p(r) dr$
End

---

Note that, in the above pseudo code, $C_1$ also has a feasible range to ensure $C-C_1$ satisfies the bounds in Eq. (43). The program was implemented in Matlab. To generate a lookup table with a fixed sample size of 100 of C for each n, n= 1, . . . , 40 and sample size of 100 of $C_1$, it takes 20 seconds in Matlab to process on a Pentium III computer.

3. Simulations

The method described above is tested using simulations. The following describes the setup parameters. It can be assumed that the dose ratio r satisfies a normalized truncated normal distribution p(r) that has the mean ½ and the standard deviation σ ranging from 0 to 1 with 0.05 increments, i.e.

$$p(r) = \frac{\exp\left(-\left(r - \frac{1}{2}\right)^2 / (2\sigma^2)\right)}{\int_0^1 \exp\left(-\left(r - \frac{1}{2}\right)^2 / (2\sigma^2)\right) dr} \text{ for } 0 \leq r \leq 1 \quad (44)$$

where $\sigma \in \{0, 0.05, 0.1, 0.15, \ldots, 0.95, 1\}$ The dose ratio is discretized into 100 numbers and a set of 40 ratios is randomly generated for each simulation according to the distribution of Eq. (44). The tumor $\alpha/\beta$ ratio is fixed for all simulations $(\alpha/\beta)_T=10$. The constraint includes the tumor BED and the maximal and the minimal fraction size. The tumor BED is obtained by using a fixed fraction size of two.

$$\text{tumor } BED = 40 \cdot \left(2 + \frac{2^2}{(\alpha/\beta)_T}\right), \text{ where } (\alpha/\beta)_T = 10 \quad (45)$$

Figure 14:
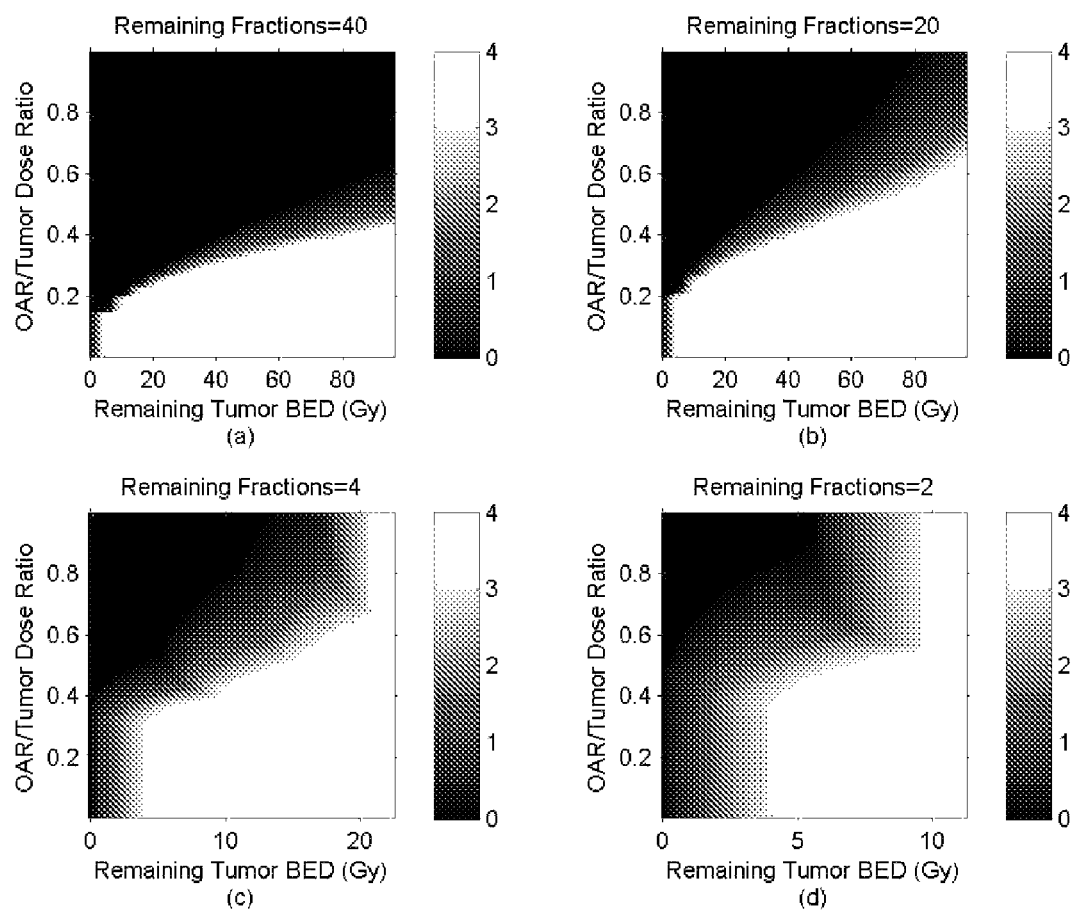
FIG. 14 illustrates plots of dose values as functions of remaining tumor BED, OAR/tumor dose ratio and the number of remaining fractions.

That is, tumor BED=96 Gy. For all cases, minimal fraction size is 0 and the maximal fraction size is either 4 or 10. However, different $(\alpha/\beta)_R$, σ and $d_{max}$ combinations can be experimented with. For each triplet of $(\alpha/\beta)_R$, σ and $d_{max}$ values, 10,000 simulations (10,000 sets of 40 ratios) are used to compute the statistics. For fixed $(\alpha/\beta)_R$, σ and $d_{max}$, a dose value lookup table is first generated. FIG. 14 ($(\alpha/\beta)_R=2$, σ=0.2 and $d_{max}=4$) and FIG. 15 ($(\alpha/\beta)_R=2$, σ=0.2 and $d_{max}=10$) show examples of the lookup tables in image plots. Then, in each simulation, the fraction size can be determined for each fraction depending on what ratio is encountered. The following data is from a sample simulation ($(\alpha/\beta)_R=2$, σ=0.2 and $d_{max}=4$). At the end of 40 fractions, the OAR BED is improved from 64.89 Gy to 39.48 Gy if using adaptive fractionation instead of using regular fractionation.

TABLE 2

| | | Adaptive Fractionation (dMax = 4 Gy) | | | Regular Fractionation (2 Gy/Frac) | | |
|---|---|---|---|---|---|---|---|
| Fraction # | Dose Ratio | Fraction Size (Gy) | OAR BED (Gy) | Tumor BED (Gy) | Fraction Size (Gy) | OAR BED (Gy) | Tumor BED (Gy) |
| 1 | 0.78 | 0.00 | 0.00 | 0.00 | 2.00 | 2.79 | 2.40 |
| 2 | 0.12 | 4.00 | 0.59 | 5.60 | 2.00 | 3.05 | 4.80 |
| 3 | 0.87 | 0.00 | 0.59 | 5.60 | 2.00 | 6.32 | 7.20 |
| 4 | 0.50 | 1.27 | 1.41 | 7.03 | 2.00 | 7.80 | 9.60 |
| 5 | 0.36 | 4.00 | 3.85 | 12.63 | 2.00 | 8.76 | 12.00 |
| 6 | 0.38 | 4.00 | 6.49 | 18.23 | 2.00 | 9.80 | 14.40 |
| 7 | 0.54 | 0.54 | 6.82 | 18.79 | 2.00 | 11.44 | 16.80 |
| 8 | 0.62 | 0.04 | 6.84 | 18.83 | 2.00 | 13.46 | 19.20 |
| 9 | 0.26 | 4.00 | 8.40 | 24.43 | 2.00 | 14.11 | 21.60 |
| 10 | 0.56 | 0.32 | 8.60 | 24.76 | 2.00 | 15.88 | 24.00 |
| 11 | 0.23 | 4.00 | 9.92 | 30.36 | 2.00 | 16.44 | 26.40 |
| 12 | 0.84 | 0.00 | 9.92 | 30.36 | 2.00 | 19.54 | 28.80 |
| 13 | 0.59 | 0.17 | 10.03 | 30.53 | 2.00 | 21.43 | 31.20 |
| 14 | 0.40 | 4.00 | 12.87 | 36.13 | 2.00 | 22.54 | 33.60 |
| 15 | 0.51 | 0.92 | 13.44 | 37.13 | 2.00 | 24.06 | 36.00 |

TABLE 2-continued

| | | Adaptive Fractionation (dMax = 4 Gy) | | | Regular Fractionation (2 Gy/Frac) | | |
|---|---|---|---|---|---|---|---|
| Fraction # | Dose Ratio | Fraction Size (Gy) | OAR BED (Gy) | Tumor BED (Gy) | Fraction Size (Gy) | OAR BED (Gy) | Tumor BED (Gy) |
| 16 | 0.61 | 0.10 | 13.50 | 37.23 | 2.00 | 26.04 | 38.40 |
| 17 | 0.61 | 0.17 | 13.61 | 37.40 | 2.00 | 28.02 | 40.80 |
| 18 | 0.56 | 0.61 | 14.01 | 38.04 | 2.00 | 29.78 | 43.20 |
| 19 | 0.56 | 0.73 | 14.50 | 38.82 | 2.00 | 31.55 | 45.60 |
| 20 | 0.51 | 1.65 | 15.68 | 40.74 | 2.00 | 33.07 | 48.00 |
| 21 | 0.67 | 0.17 | 15.80 | 40.91 | 2.00 | 35.32 | 50.40 |
| 22 | 0.54 | 1.46 | 16.89 | 42.59 | 2.00 | 36.96 | 52.80 |
| 23 | 0.68 | 0.28 | 17.09 | 42.87 | 2.00 | 39.26 | 55.20 |
| 24 | 0.18 | 4.00 | 18.06 | 48.47 | 2.00 | 39.68 | 57.60 |
| 25 | 0.70 | 0.20 | 18.21 | 48.67 | 2.00 | 42.08 | 60.00 |
| 26 | 0.37 | 4.00 | 20.75 | 54.27 | 2.00 | 43.08 | 62.40 |
| 27 | 0.49 | 2.80 | 23.03 | 57.86 | 2.00 | 44.52 | 64.80 |
| 28 | 0.65 | 0.43 | 23.35 | 58.30 | 2.00 | 46.68 | 67.20 |
| 29 | 0.42 | 4.00 | 26.40 | 63.90 | 2.00 | 47.86 | 69.60 |
| 30 | 0.53 | 1.72 | 27.71 | 65.93 | 2.00 | 49.46 | 72.00 |
| 31 | 0.24 | 4.00 | 29.11 | 71.53 | 2.00 | 50.05 | 74.40 |
| 32 | 0.95 | 0.00 | 29.11 | 71.53 | 2.00 | 53.76 | 76.80 |
| 33 | 0.43 | 4.00 | 32.27 | 77.13 | 2.00 | 54.97 | 79.20 |
| 34 | 0.19 | 4.00 | 33.30 | 82.73 | 2.00 | 55.42 | 81.60 |
| 35 | 0.62 | 0.28 | 33.49 | 83.01 | 2.00 | 57.44 | 84.00 |
| 36 | 0.57 | 0.93 | 34.16 | 84.02 | 2.00 | 59.25 | 86.40 |
| 37 | 0.30 | 4.00 | 36.06 | 89.62 | 2.00 | 60.02 | 88.80 |
| 38 | 0.43 | 2.72 | 37.89 | 93.08 | 2.00 | 61.23 | 91.20 |
| 39 | 0.43 | 2.08 | 39.16 | 95.59 | 2.00 | 62.45 | 93.60 |
| 40 | 0.70 | 0.40 | 39.48 | 96.00 | 2.00 | 64.84 | 96.00 |

4. Results

Figure 15:
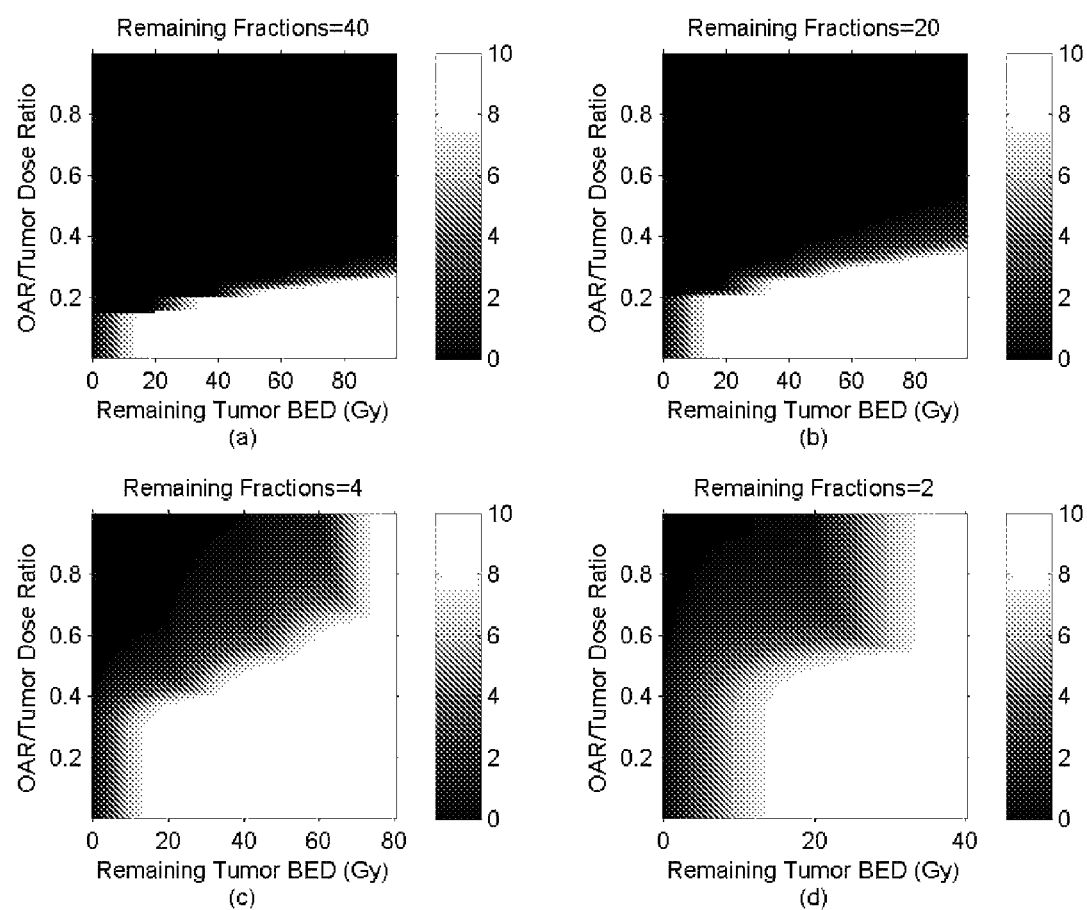
FIG. 15 illustrates plots of dose values as functions of remaining tumor BED, OAR/tumor dose ratio and the number of remaining fractions.
Figure 16:
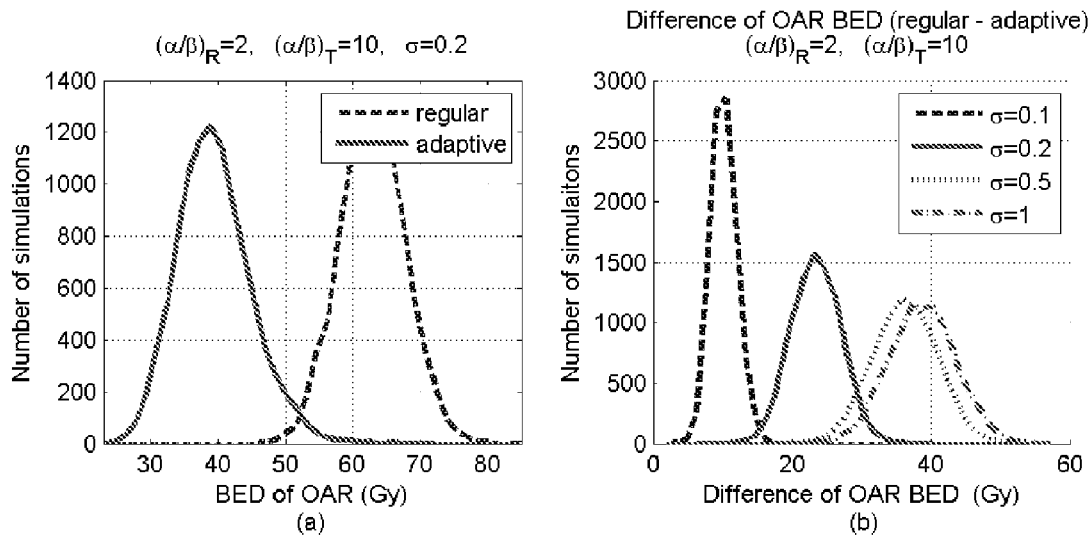
FIG. 16 (*a*) illustrates OAR BED distributions using 10,000 simulations for both the adaptive fractionation and the regular fractionation, while (b) illustrates the distributions of their difference (regular-adaptive) for different A's.
Figure 17:
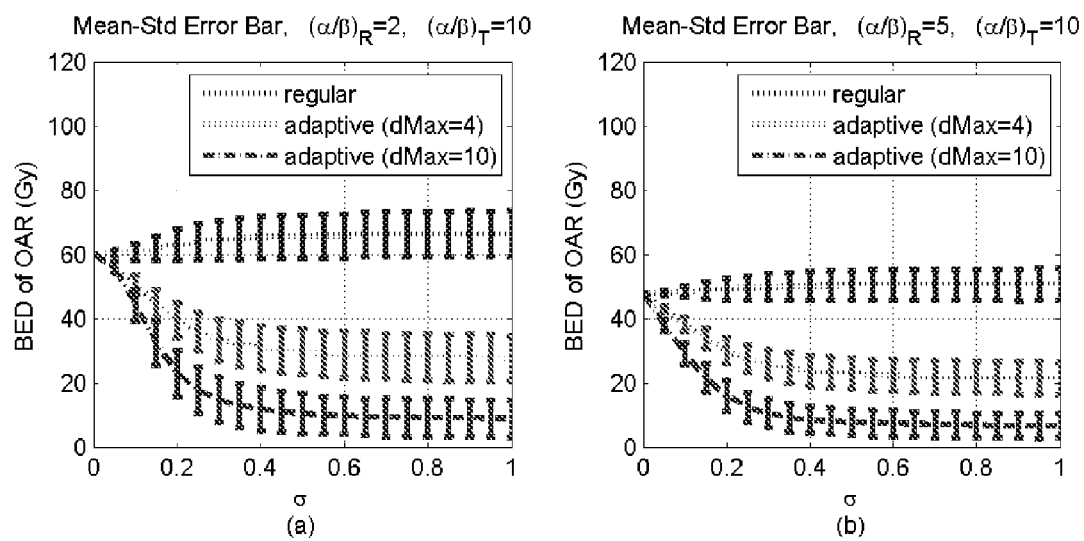
FIG. 17 illustrates condensed plots of the information of FIG. 16 including all σ values.

FIGS. 14 and 15 are image plots of dose values as functions of remaining tumor BED, OAR/tumor dose ratio and the number of remaining fractions. The images show that the transition area (the area with dose values between 0 and maximum) gets larger as the number of remaining fractions gets smaller. In other words, at the beginning of the treatment, the adaptation strategy is to deliver mostly zero or maximal fraction size; as the treatment proceeds, more intermediate fraction sizes are needed. FIG. 16(a) graphically illustrates OAR BED distributions using 10,000 simulations for both the adaptive fractionation and the regular fractionation. FIG. 16(b) graphically illustrates the distributions of their difference (regular-adaptive) for different σ's. FIG. 17 illustrates condensed plots of FIG. 16 including all σ values. As σ increases, the mean and the standard deviation stabilize because the probability distribution of the OAR/tumor dose ratios stabilize too. FIG. 17 also indicates that, the larger the maximal allowable dose, the better the adaptive fractionation performs.

5. Discussion

It is evident that adaptive fractionation improves the normal tissue sparing both theoretically and numerically. The simulations also show that adaptive fractionation is better than regular fractionation (FIG. 16(b)). The proposed method can be applied to a more general form of BED including the proliferation factors by simply modify the BED formulations of the objective and the constraint.

6. Conclusion

In the adaptive fractionation strategy proposed in this section, a fraction size lookup table is built up inductively from the single fraction case and the computation is done off-line. This lookup table can be used for on-line fraction size determination once the dose ratio is available for the current fraction. In addition, the fraction size lookup table can also be recomputed if the dose ratio distribution is updated. Extensive simulations demonstrate the efficacy and robustness of the proposed adaptation strategy. For a typical 20% dose ratio variation and the fraction size bound [0 4] (Gy), the gain of OAR sparing is around 20% compared with conventional fractionation.

7. Appendix

The survival curves $S_T$ for tumor cells can be modeled using linear-quadratic functions.

$$S_T = \exp\left(-\left(\alpha_T D + \beta_T \frac{D^2}{N}\right)\right) \tag{46}$$

where $\alpha_T$ and $\beta_T$ are constant for the linear and quadratic terms respectively, and N is the number of fractions. Similarly, the survival curve $S_R$ for normal tissues can be expressed as $$S_R = \exp\left(-\left(\alpha_R D + \beta_R \frac{D^2}{N}\right)\right) \tag{47}$$

The $\alpha/\beta$ ratio is higher for tumor cells and lower for normal tissues. By increasing the number of fractions, the survival of normal tissues can be increased while the tumor cell kill can be maintained. Taking log followed by the first derivative on Eq. (46), yields $$0 = \alpha_T \frac{dD}{dN} + \beta_T \left(\frac{2D\frac{dD}{dN}}{N} - \frac{D}{N^2}\right) \tag{48}$$

If the same method is performed on Eq. (47), the result is $$-\frac{d(\log S_R)}{dN} = \alpha_R \frac{dD}{dN} + \beta_R \left(\frac{2D\frac{dD}{dN}}{N} - \frac{D}{N^2}\right) \tag{49}$$

Multiplying $\beta_T$ by (49) and $\beta_R$ by (48) and subtracting the latter from the former, yields $$-\beta_T \frac{d(\log S_R)}{dN} = (\alpha_R \beta_T - \alpha_T \beta_R)\frac{dD}{dN} \tag{50}$$

or $$\frac{d(\log S_R)}{dN} = \beta_R\left(\frac{\alpha_T}{\beta_T} - \frac{\alpha_R}{\beta_R}\right)\frac{dD}{dN} \tag{51}$$

From Eq. (46), it is known that if $S_T$ holds constant, then D is an increasing function of N. That is, $$\frac{dD}{dN} > 0 \tag{52}$$

And equation Eq. (51) illustrates that $\log S_R$ is also an increasing function of N if the $\alpha/\beta$ ratio of the tumor cells is greater. In other words, the survival of normal tissues increases by keeping the tumor cell kill and increasing the number of fractions.

III. Adaptive Fractionation Using Decision Tree

This section presents a decision tree type strategy to determine the fraction size according to the configurations and their probability of occurrence. We also demonstrate the effectiveness of this proposed method by showing the closeness of its result to that of the gold standard using numerical simulations.

In radiation therapy, the goal is to deliver at least the prescribed dose to the tumor and minimize the dose received by the organ at risk (OAR) by the elaborate IMRT treatment plan. After treatment planning, the entire volume of interest (VOI) has a dose map and the dose ratio of each region to the tumor according to the dose map can be determined. The dose ratio of a region to the tumor is the number r that if the tumor receives dose d, then that region receives dose dr. For biological reasons, a whole treatment is divided into multiple fractions where the fraction sizes times the dose delivered in each fraction, sum up to the total dose. As previously discussed, the fraction sizes are equal in conventional fractionation therapy. However, the OAR/tumor dose ratio, or simply the dose ratio, may change for different fractions due to the change of the relative position (configuration) of the OAR and the tumor. Intuitively, if fewer doses are delivered when the dose ratio is higher and more doses when the dose ratio is lower, the average dose ratio can be reduced and the total dose at the end maintained. In fact, in retrospective study, we can set up a linear programming problem that finds the optimal fraction sizes given the OAR/tumor dose ratios for each fraction.

In this section, a decision-tree strategy is presented which can determine the fraction size assuming there are finitely many configurations and the probability of the occurrence of each configuration is known. The strategy is to minimize the expected dose ratio. Simulations have been run to compare this method with the gold standard (the retrospective study). In the discussion section, the practicality and the limitation of the proposed method is discussed.

1. Method

A decision-tree type method usually applies on problems with a finite number of nodes and the answer is built up inductively from the last stage. In this case, there are a finite number of fractions and the answer will be built up starting from the one fraction case. The basic assumptions are (i) the patient has N possible configurations; (ii) the OAR/tumor dose ratio $r_i$ for the i-th configuration is known; (iii) the probability $p_i$ of the occurrence of the i-th configuration is known. Based on these assumptions, a solution can be obtained that minimizes the OAR dose in the sense of expectation and maintains the total dose for the tumor.

The following notations are used in this section:

L, the total number of fractions
$D_L$, the total dose for L fractions
$d_{max}$, maximal fraction size
$d_{min}$, minimal fraction size
$d_i$, dose delivered at the i-th fraction
N, the number of configurations
$r_i$, the dose ratio for the i-th configuration
$p_i$, probability of the occurrence of the i-th configuration
r, a random variable whose value is in $\{r_1, \ldots, r_N\}$
$\langle r \rangle$, the expectation of r, i.e.

$$\langle r \rangle = \sum_{i=1}^{N} p_i r_i$$

$r^{(l)}$, $l=1, 2, \ldots$, inductively defined random variables for non-constrained cases and $r^{(1)}=r$
$r^{(m,k)}$, $m=1, 2, \ldots$ and $k=1, \ldots, m$, inductively defined random variables for constrained cases and $r^{(1,1)}=r$.

The problem can be stated as follows:

Given that there are L fractions and the total dose is $D_L$, how much dose should be delivered for the first fraction if the OAR is at the i-th configuration and the fraction sizes are limited between $d_{min}$ and $d_{max}$ for all fractions?

The solution is given below:

For each fraction m, $m=1, \ldots, L-1$, inductively define a sequence of random variables $r^{(m,k)}$, $k=1, \ldots, m$. Next, find l such that $$(l-1)(d_{max}-d_{min}) \leq D_L - L d_{min} \leq l(d_{max}-d_{min}) \tag{53}$$

Then the fraction size for the first fraction is $$d_1 = \begin{cases} d_{max} & \text{if } r_i \leq \langle r^{(L-1,l-1)} \rangle \\ D_L - (L-l)d_{min} - (l-1)d_{max} & \text{if } \langle r^{(L-1,l-1)} \rangle < r_i \leq \langle r^{(L-1,l)} \rangle \\ d_{min} & \text{if } \langle r^{(L-1,l)} \rangle < r_i \end{cases} \tag{54}$$

Note that it is sufficient to determine the fraction size for the first fraction. Equivalently, the total dose $D_L$ can be decomposed into L numbers in the decreasing order.

$$D_L = \underbrace{d_{max} + \ldots + d_{max}}_{l-1} + \left( \begin{array}{c} D_L - (l-1)d_{max} - \\ (L-l)d_{min} \end{array} \right) + \underbrace{d_{min} + \ldots + d_{min}}_{L-l} \tag{55}$$

The expectations $\langle r^{(L-1,k)} \rangle$, $k=1, \ldots, L-1$, also divide the $r_i$'s range into L intervals. For each interval from the smaller values to the larger values (left to right), a number is associated in Eq. (55) in that decreasing order. Then, the fraction size is the number associated to the interval in which the dose ratio of the observed configuration falls. In other words, the fraction size is either $d_{max}$, $d_{min}$ or the remaining.

The problem and solution given above are actually a simple generalization of the case where $d_{min}=0$. The random variables $r^{(m,k)}$, $k=1, \ldots, m$ are defined inductively by $$r_j^{(m,k)} = \begin{cases} \langle r^{(m-1,k-1)} \rangle & \text{when } r_j \leq \langle r^{(m-1,k-1)} \rangle \\ r_j & \text{when } \langle r^{(m-1,k-1)} \rangle < r_j \leq \langle r^{(m-1,k)} \rangle \\ \langle r^{(m-1,k)} \rangle & \text{when } \langle r^{(m-1,k)} \rangle \leq r_j \end{cases} \tag{56}$$

$r^{(1,1)}=r$ and the probability of $r_j^{(m,k)}$ is $p_j$. The quantity $D_L - L d_{min}$ is in the range $0 \leq D_L - L d_{min} \leq L(d_{max}-d_{min})$. Therefore, it must be in one of the L intervals as in Eq. (53). Then, these two numbers $\langle r^{(L-1,l-1)} \rangle$ and $\langle r^{(L-1,l)} \rangle$ are used as the threshold for the dose ratio and the fraction size is determined according to Eq. (54). For the remainder of this section, the non-constrained case (without upper bounds and $d_{min}=0$) and the constrained case are described for a few fractions. The inductive proof for higher fractions is given in the Appendix.

(i) Non-Constrained Case (without Upper Bounds for Each Fraction)

Suppose there are two fractions. From the viewpoint of fraction one, the expected OAR dose is $$d_1 r_i + (D - d_1)\langle r \rangle = d_1(r_i - \langle r \rangle) + D\langle r \rangle \tag{57}$$

To minimize Eq. (57), the following parameters are set:

$$d_1 = \begin{cases} D, & r_i \leq \langle r \rangle \\ 0, & r_i > \langle r \rangle \end{cases} \quad (58)$$

Note that at the boundary $r_i = \langle r \rangle$, both choices $d_1=0$ and $d_1=D$ minimize (57). The choice in Eq. (58) is subjective, but is fixed for the sake of consistency. However, its impact should be reviewed. Thus, the expected OAR dose for these two fractions is $$\sum_{i \in I} p_i D r_i + \sum_{i \in I'} p_i D \langle r \rangle \quad (59)$$

where $I = \{i | r_i \leq \langle r \rangle\}$ and $I'$ is the complement of $I$. The expectation in Eq. (59) can also be written as $$D \langle r^{(2)} \rangle, \text{ where } r_i^{(2)} = \begin{cases} r_i, & r_i \leq \langle r \rangle \\ \langle r \rangle, & r_i > \langle r \rangle \end{cases} \quad (60)$$

and the probability $p_i$ is assigned to $r_i^{(2)}$. A similar statement about the optimal choice of dose delivery, the formulation of OAR dose expectation and the construction of the auxiliary dose ratio sequence for the threshold purpose can be generalized to higher fraction numbers and proved by mathematical induction. The statement for general L is given below:

(S.1) The optimal delivery is either all or none.

$$d_1 = \begin{cases} D_L & r_i \leq \langle r^{(L-1)} \rangle \\ 0 & r_i > \langle r^{(L-1)} \rangle \end{cases} \quad (61)$$

(S.2) The expectation of the OAR dose is $$D_L \langle r^{(L)} \rangle, \text{ where } r_i^{(L)} = \begin{cases} r_i, & r_i \leq \langle r^{(L-1)} \rangle \\ \langle r^{(L-1)} \rangle, & r_i > \langle r^{(L-1)} \rangle \end{cases} \quad (62)$$

and the probability for $r^{(L)} = r_i^{(L)}$ is $p_i$.

(S.1) and (S.2) have been proved for $L=2$. Larger L can be proved by mathematical induction and is given in the Appendix. Note that it is sufficient to determine the dose for the first fraction. In summary, the delivery strategy when there is no upper bound for the dose in each fraction is to deliver all or none.

(ii) Constrained Case (with Upper Bounds for Each Fraction)

Next, the following constraint is added $$d_l \leq d_{max} \forall l = 1, \ldots, L \quad (63)$$

to study the strategy, with $L=2$ again. The total dose $D_2$ is broken into two cases: (i) $0 \leq D_2 \leq d_{max}$ and (ii) $d_{max} \leq D_2 \leq 2d_{max}$. Note that though the two cases have overlapped endpoints, the result is consistent regardless of which case is applied. For case (i), the result is the same as that of the no constraint case. So, only case (ii) is reviewed below. From the viewpoint of the first fraction, the expected OAR dose is the same as Eq. (57). To minimize it, the following parameter is set:

$$d_1 = \begin{cases} d_{max}, & r_i \leq \langle r \rangle \\ D - d_{max}, & r_i > \langle r \rangle \end{cases} \quad (64)$$

Thus, the expected OAR dose is $$\sum_{i \in I} p_i (d_{max} r_i + (D - d_{max}) \langle r \rangle) + \sum_{i \in I'} p_i ((D - d_{max}) r_i + d_{max} \langle r \rangle) = \quad (65)$$

$$d_{max} \left( \sum_{i \in I} p_i r_i + \sum_{i \in I'} p_i \langle r \rangle \right) + (D - d_{max}) \left( \sum_{i \in I} p_i \langle r \rangle + \sum_{i \in I'} p_i r_i \right) =$$

$$d_{max} \langle r^{(2,1)} \rangle + (D - d_{max}) \langle r^{(2,2)} \rangle$$

where $r^{(2,1)}$ and $r^{(2,2)}$ are new random variables defined through $r$.

$$r_j^{(2,1)} = \begin{cases} r_j & \text{for } r_j \leq \langle r \rangle \\ \langle r \rangle & \text{for } r_j > \langle r \rangle \end{cases} \quad (66)$$

and $$r_j^{(2,2)} = \begin{cases} \langle r \rangle & \text{for } r_j \leq \langle r \rangle \\ r_j & \text{for } r_j > \langle r \rangle \end{cases} \quad (67)$$

and the probability $p_i$ is assigned to both $r_j^{(2,1)}$ and $r_j^{(2,2)}$. It can be seen that $\langle r^{(2,1)} \rangle \leq \langle r^{(2,2)} \rangle$. The general statement for the constrained case is (S.3) The total dose $D_L$ can be in any of the L segments:

$$(l-1)d_{max} < D_L \leq l d_{max} \quad l=1, \ldots, L \quad (68)$$

For $D_L$ in the l-th segment, the optimal delivery is $$d_1 = \begin{cases} d_{max} & \text{when } r_i \leq \langle r^{(L-1, l-1)} \rangle \\ D_L - (l-1)d_{max} & \text{when } \langle r^{(L-1, l-1)} \rangle < r_i \leq \langle r^{(L-1, l)} \rangle \\ 0 & \text{when } \langle r^{(L-1, l)} \rangle < r_i \end{cases} \quad (69)$$

(S.4) The expectation of the OAR dose is $$\sum_{k=1}^{l-1} d_{max} \langle r^{(L,k)} \rangle + (D_L - (l-1)d_{max}) \langle r^{(L,l)} \rangle \quad (70)$$

for $(l-1)d_{max} \leq D_L \leq l d_{max}$

And the random variables $r^{(L,k)}$, $k=1, \ldots, L$ are defined as follows. First, the random variables $r^{(L-1,k)}$, $k=1, \ldots, L-1$ defines L−1 numbers $\langle r^{(L-1,k)} \rangle$, $k=1, \ldots, L-1$, which in turn determine L intervals on the range of $\{r_i\}_{i=1, \ldots, N}$. Now, the following can be defined $$r_j^{(L,k)} = \begin{cases} \langle r^{(L-1,k-1)} \rangle & \text{when } r_j \leq \langle r^{(L-1,k-1)} \rangle \\ r_j & \text{when } \langle r^{(L-1,k-1)} \rangle < r_j \leq \langle r^{(L-1,k)} \rangle \\ \langle r^{(L-1,k)} \rangle & \text{when } \langle r^{(L-1,k)} \rangle \leq r_j \end{cases} \quad (71)$$

In addition, the probability $p_j$ is assigned to $r_i^{(L,k)} \forall k=1, \ldots, L$. It follows from the definition Eq. (71) that $$\langle r^{(L,1)} \rangle \leq \langle r^{(L,2)} \rangle \leq \ldots \leq \langle r^{(L,L)} \rangle \quad (72)$$

(S.3) and (S.4) have been proved for $L=2$. Larger L are proved by mathematical induction (given in the Appendix). Note that it is sufficient to determine the dose for the first fraction.

In order to summarize the delivery scheme, suppose there are L fractions and the total dose $D_L$ is in the range (l-1)$d_{max} < D_L \leq l d_{max}$ for some $l \in \{1, 2, \ldots, L\}$. Then the optimal fraction size is $$d_1 = \begin{cases} d_{max} & \text{if } r_i \leq \langle r^{(L-1,l-1)} \rangle \\ D_L - (l-1)d_{max} & \text{if } \langle r^{(L-1,l-1)} \rangle < r_i \leq \langle r^{(L-1,l)} \rangle \\ 0 & \text{if } \langle r^{(L-1,l)} \rangle < r_i \end{cases} \quad (73)$$

assuming the OAR is at the i-th configuration. An alternative way of looking at this is to decompose the total dose $D_L$ into L numbers.

$$\underbrace{d_{max}, \ldots, d_{max}}_{l-1}, D - (l-1)d_{max}, 0, \ldots, 0 \quad (74)$$

The random variables $\{r^{(L-1,k)}\}_{k=1,\ldots,L-1}$ define L-1 numbers $\{\langle r^{(L-1,k)} \rangle\}_{k=1,\ldots,L-1}$, which divides the dose ratio range into L intervals. The optimal dose is obtained by using the numbers in Eq. (74) the same order in which interval the dose ratio $r_i$ is provided.

This delivery scheme can be generalized to the problem with both upper and non-zero lower bound dose constraints $$d_{min} \leq d_l \leq d_{max} \forall l=1, \ldots, L \quad (75)$$

This is accomplished by re-defining a new maximal dose $d'_{max} = d_{max} - d_{min}$ and changing the total dose for L fractions from $D_L$ to $D'_L = D_L - L d_{min}$. Then, at each fraction, the delivery $d'_l$ is optimized subject to the constraint $$0 \leq d'_l = d_l - d_{min} \leq d'_{max} = d_{max} - d_{min} \forall l=1, \ldots, L \quad (76)$$

The problem is then reduced to the previous case.

2. Discussion and Conclusion

This approach relies on the availability of the probability of occurrence of configurations to maximize OAR sparing while maintaining tumor dose. The probability of the occurrence of configurations can be estimated from the patient history. When the configuration change is too large, re-optimization may be necessary.

3. Appendix (i) Proof of (S.1) and (S.2)

The statements (S.1) and (S.2) are proved by mathematical induction. It has been shown that Equations (61) and (62) are true for L=2. Assume they are true for L-1. It can be proved that Equations (61) and (62) hold for L, which will complete the proof. Suppose there are L fractions. From the view point of the first fraction, the expected error is $$d_1 r_i + (D_L - d_1)\langle r^{(L-1)} \rangle = d_1(r_i - \langle r^{(L-1)} \rangle) + D_L \langle r^{(L-1)} \rangle \quad (77)$$

To minimize (77), the dose for the first fraction should be $$d_1 = \begin{cases} D_L, & r_i \leq \langle r^{(L-1)} \rangle \\ 0, & r_i > \langle r^{(L-1)} \rangle \end{cases} \quad (78)$$

Therefore, the expected OAR dose for L fractions is $$\sum_{i \in \{i | r_i \leq \langle r^{(L-1)} \rangle\}} p_i D_L r_i + \sum_{i \in \{i | r_i \leq \langle r^{(L-1)} \rangle\}} p_i D_L \langle r^{(L-1)} \rangle \quad (79)$$

which can be written as $$D_L \langle r^{(L)} \rangle, \text{ where } r_i^{(L)} = \begin{cases} r_i, & r_i \leq \langle r^{(L-1)} \rangle \\ \langle r^{(L-1)} \rangle, & r_i > \langle r^{(L-1)} \rangle \end{cases} \quad (80)$$

and the probability for $r^{(L)} = r_i^{(L)}$ is $p_i$.

(ii) Proof of (S.3) and (S.4)

Similar to the proof of (S.1) and (S.2), mathematical induction can be used to prove (S.3) and (S.4). It has been shown that (S.3) and (S.4) are true for L=2. Assume they are true for L-1 fractions, and the objective is to prove it for L fractions. Now suppose there are L fractions and the total dose $D_L$ is in the range (l-1)$d_{max} < D_L \leq l d_{max}$ for some $l \in \{1, 2, \ldots, L\}$. From the viewpoint of the first fraction, the expected OAR dose is $$d_1 r_i + \begin{cases} \sum_{k=1}^{l-2} d_{max} \langle r^{(L-1,k)} \rangle + (D_L - d_1 - (l-2)d_{max})\langle r^{(L-1,l-1)} \rangle \\ \quad \text{if } (l-2)d_{max} \leq D_L - d_1 \leq (l-1)d_{max} \\ \sum_{k=1}^{l-1} d_{max} \langle r^{(L-1,k)} \rangle + (D_L - d_1 - (l-1)d_{max})\langle r^{(L-1,l)} \rangle \\ \quad \text{if } (l-1)d_{max} \leq D_L - d_1 \leq l d_{max} \end{cases} \quad (81)$$

To minimize Eq. (81), the fraction size should be $$d_1 = \begin{cases} d_{max} & \text{when } r_i \leq \langle r^{(L-1,l-1)} \rangle \\ D_L - (l-1)d_{max} & \text{when } \langle r^{(L-1,l-1)} \rangle < r_i \leq \langle r^{(L-1,l)} \rangle \\ 0 & \text{when } \langle r^{(L-1,l)} \rangle < r_i \end{cases} \quad (82)$$

Thus the expected error is $$\sum_{\substack{i \in \{i | r_i \leq \langle r^{(L-1,l-1)} \rangle\} \\ I_1 \cup \ldots \cup I_{l-1}}} p_i \left( d_{max} r_i + \sum_{k=1}^{l-2} d_{max} \langle r^{(L-1,k)} \rangle + (D_L - (l-1)d_{max})\langle r^{(L-1,l-1)} \rangle \right) + \\
\sum_{i \in \{i | \langle r^{(L-1,l-1)} \rangle < r_i \leq \langle r^{(L-1,l)} \rangle\} = I_l} p_i \left( (D_L - (l-1)d_{max})r_i + \sum_{k=1}^{l-1} d_{max} \langle r^{(L-1,k)} \rangle \right) + \\
\sum_{\substack{i \in \{i | \langle r^{(L-1,l)} \rangle < r_i\} \\ I_{l+1} \cup \ldots \cup I_L}} p_i \left( \sum_{k=1}^{l-1} d_{max} \langle r^{(L-1,k)} \rangle + (D_L - (l-1)d_{max})\langle r^{(L-1,l)} \rangle \right) = \\
d_{max} \left( \sum_{i \in I_1} p_i r_i + \sum_{i \in I_2 \cup \ldots \cup I_L} p_i \langle r^{(L-1,1)} \rangle \right) + \quad (83)$$

-continued $$d_{max}\left(\sum_{i\in I_1} p_i\langle r^{(L-1,1)}\rangle + \sum_{i\in I_2} p_i r_i + \sum_{i\in I_3\cup\ldots\cup I_L} p_i\langle r^{(L-1,2)}\rangle\right) +$$

$$d_{max}\left(\sum_{i\in I_1\cup I_2} p_i\langle r^{(L-1,2)}\rangle + \sum_{i\in I_3} p_i r_i + \sum_{i\in I_4\cup\ldots\cup I_L} p_i\langle r^{(L-1,3)}\rangle\right) \vdots +$$

$$d_{max}\left(\sum_{i\in I_1\cup\ldots\cup I_{l-2}} p_i\langle r^{(L-1,l-2)}\rangle + \sum_{i\in I_{l-1}} p_i r_i + \sum_{i\in I_l\cup\ldots\cup I_L} p_i\langle r^{(L-1,l-1)}\rangle\right) +$$

$$(D_L - (l-1)d_{max})\left(\sum_{i\in I_1\cup\ldots\cup I_{l-1}} p_i\langle r^{(L-1,l-1)}\rangle + \sum_{i\in I_l} p_i r_i + \sum_{i\in I_{l+1}\cup\ldots\cup I_L} p_i\langle r^{(L-1,l)}\rangle\right) =$$

$$d_{max}\langle r^{(L,1)}\rangle + d_{max}\langle r^{(L,2)}\rangle + \ldots + d_{max}\langle r^{(L,l-1)}\rangle + (D_L - (l-1)d_{max})\langle r^{(L,l)}\rangle$$

And the random variables $r^{(L,k)}$ for $k=1, \ldots, L$ are defined as in Eq. (71). This completes the induction step.

IV. Adaptive Fractionation with Biological Model

In this section, a biological model type of adaptation is presented assuming the OAR/tumor dose ratios and the probability of their occurrence are known. In the previous section, we discussed adaptation without biological formulation—the objective being to minimize the OAR dose and the constraint being to maintain the tumor dose. Unlike the previous optimization approach, a fraction size lookup table is built from bottom up for each fraction with the remaining tumor control (TC) and the current dose ratio as inputs. The fraction size for the current fraction is determined by maximizing the future expected survival of OAR and preserving the TC. Simulations demonstrate the effectiveness of this method as compared to the equal fraction size method.

Radiation therapy can be fractionized to increase the normal tissue sparing and maintain the same level of tumor cell kill simultaneously when both survival curves are described using the linear quadratic model and the α/β ratio of tumor is higher (see Appendix). In the previous section, adaptation was studied without the use of biological modeling—both objective functions and constraints were just total doses. The adaptation was formulated to minimize the OAR dose and to preserve the tumor dose. In this section, the objective function is defined to be the survival of OAR with the constraint to be the tumor kill—both in linear-quadratic models. Like the assumptions used in the previous section, it is assumed that the OAR/tumor dose ratios satisfy a normal distribution. An expected optimum (derived from the maximal OAR survival curve) can then be inductively defined with the constraint being the tumor cell kill. In each inductive step, the fraction size is constructed as a function of dose ratio and the remaining tumor cell kill (described in further detail below). Simulations are used to compare this method with the equal fraction size method. The thus built fraction size can be used as a look-up table for on-line determination.

The following is a list of notations that are used throughout this section:
N, the number of fractions
$d_i$, dose at the i-th fraction
$r_i$, OAR/tumor dose ratio at the i-th fraction
$\alpha_R$, the constant of the linear term for the OAR survival curve
$\beta_R$, the constant of the quadratic term for the OAR survival curve
$\alpha_T$, the constant of the linear term for the tumor kill
$\beta_T$, the constant of the quadratic term for the tumor kill 1. Method The linear-quadratic model for the survival curve is $$S_T = \exp(-(\alpha_T d + \beta_T d^2)) \quad (84)$$

and $$S_R = \exp(-(\alpha_R d + \beta_R d^2)) \quad (85)$$

for the tumor and OAR, respectively, if they receive dose d. If the fraction sizes are $\{d_1, \ldots, d_N\}$, then the resulting tumor survival is $$S_T = \exp\left(-\sum_{i=1}^{N}(\alpha_T d_i + \beta_T d_i^2)\right) \quad (86)$$

The adaptive fractionation problem is to determine $\{d_1, \ldots, d_N\}$ so that the tumor survival in Eq. (86) is a constant while the OAR survival is maximized.

$$S_R = \exp\left(-\sum_{i=1}^{N}(\alpha_R d_i r_i + \beta_R (d_i r_i)^2)\right) \quad (87)$$

Alternatively, the problem can be formulated as $$\min_{\{d_1,\ldots,d_N\}} \sum_{i=1}^{N} \alpha_R d_i r_i + \beta_R (d_i r_i)^2 \quad (88)$$

$$\text{subject to } \sum_{i=1}^{N} \alpha_T d_i + \beta_T d_i^2 = C$$

where C is a constant. The objective function in Eq. (88) is called the normal tissue complication (NTC), and the constraint in Eq. (88) is called the tumor control (TC).

Suppose there is only one fraction. Then the equation $$\alpha_T d_1 + \beta_T d_1^2 = C \quad (89)$$

completely determines $d_1$. In fact, $d_1$ can be written as a function of C.

$$d_1 = h(C) = \frac{-\alpha_T + \sqrt{\alpha_T^2 + 4\beta_T C}}{2\beta_T} \quad (90)$$

And the minimal NTC is $$\alpha_R d_1 r_1 + \beta_R (d_1 r_1)^2 = \alpha_R r_1 h(C) + \beta_R r_1^2 h(C)^2 \quad (91)$$

regardless of what $r_1$ is. Its expected value is also a function of C.

$$f_1(C) = \alpha_R \langle r_1 \rangle h(C) + \beta_R \langle r_1^2 \rangle h(C)^2 \quad (92)$$

$f_1(C)$ is the expected minimal NTC for any given TC C when there is only one fraction.

Suppose there are two fractions. If the TC for the first fraction is $C_1$, then the TC for the second fraction is $C-C_1$. From the viewpoint of the first fraction, the following should be minimized:

$$\min_{C_1} \alpha_R r_1 h(C_1) + \beta_R r_1^2 h(C_1)^2 + f_1(C - C_1) \quad (93)$$

For each possible value of $r_1$, there is a corresponding $C_1$ that minimizes Eq. (93). That is, such $C_1$ is a function of $r_1$ and C. And the minimum in Eq. (93) is also a function $g(r_1, C)$ of $r_1$ and C. In addition, the fraction size can be determined by $d = h(C_1)$. Therefore, the fraction size is also a function of $r_1$ and C. The expected minimal NTC is denoted by $f_2(C)$.

$$f_2(C) = \int g(r_1, C) p(r_1) dr_1 \quad (94)$$

This process can continue in the same manner.

2. Results

The method described above can be tested by simulations. It is assumed that the dose ratio r satisfies a normal distribution with mean one-half and the standard deviation one-sixteenth.

$$p(r) = \frac{1}{\sqrt{2\pi}\,\sigma} \exp\left(\frac{-\left(r - \frac{1}{2}\right)^2}{2\sigma^2}\right) \quad (95)$$

where $\sigma \frac{1}{16}$. The dose ratio is discretized into one hundred numbers. Then forty ratios are randomly generated according to this distribution.

3. Appendix

The survival curves $S_T$ for tumor cells can be modeled using linear-quadratic functions.

$$S_T = \exp\left(-\left(\alpha_T D + \beta_T \frac{D^2}{N}\right)\right) \quad (96)$$

where $\alpha_T$ and $\beta_T$ are constant for the linear and quadratic terms respectively, and N is the number of fractions. Similarly, the survival curve $S_R$ for normal tissues can be expressed as $$S_R = \exp\left(-\left(\alpha_R D + \beta_R \frac{D^2}{N}\right)\right) \quad (97)$$

The $\alpha/\beta$ ratio is higher for tumor cells and lower for normal tissues. By increasing the number of fractions, the survival of normal tissues can be increased while the tumor cell kill can be maintained. Taking log and differentiating Eq. (96) yields:

$$0 = \alpha_T \frac{dD}{dN} + \beta_T \left(\frac{2D\frac{dD}{dN}}{N} - \frac{D}{N^2}\right) \quad (98)$$

If the same operations are performed on Eq. (97), the following is obtained:

$$-\frac{d(\log S_R)}{dN} = \alpha_R \frac{dD}{dN} + \beta_R \left(\frac{2D\frac{dD}{dN}}{N} - \frac{D}{N^2}\right) \quad (99)$$

Multiplying $\beta_T$ by Eq. (99) and $\beta_R$ by Eq. (98) and subtracting, yields:

$$-\beta_T \frac{d(\log S_R)}{dN} = (\alpha_R \beta_T - \alpha_T \beta_R) \frac{dD}{dN} \quad (100)$$

or $$\frac{d(\log S_R)}{dN} = \beta_R \left(\frac{\alpha_T}{\beta_T} - \frac{\alpha_R}{\beta_R}\right) \frac{dD}{dN} \quad (101)$$

From Eq. (96), it is known that if $S_T$ holds constant, then D is an increasing function of N. That is, $$\frac{dD}{dN} > 0 \quad (102)$$

And, Eq. (101) says that $\log S_R$ is also an increasing function of N if the $\alpha/\beta$ ratio of the tumor cells is bigger. In other words, the survival of normal tissues increases when the number of fractions increases.

These various fractionation adaptation techniques can be performed by the fraction modification module 110 to optimize the treatment plan for the patient and the particular fraction of radiation dose to be delivered to the patient.

Various features and advantages of the invention are set forth in the following claims.

What is claimed is:

1. A method of adapting a treatment plan, the method comprising:
   using a computer to prepare a treatment plan for a patient, the treatment plan including multiple treatment fractions each having a planned radiation dose to be delivered to the patient;
   after the treatment plan is prepared, using a computer to identify a first position of a first structure relative to a second structure prior to delivering each one of the fractions,
   prior to delivering the present treatment fraction, using a computer to identify a second position of the first structure relative to the second structure;
   using a computer to adjust the planned radiation dose to be delivered to the patient for the present treatment fraction based on the second position of the first structure relative to the second structure without replanning the treatment plan; and
   delivering the adjusted planned radiation dose to the patient with a radiation delivery device.

2. The method of claim 1, wherein the first structure includes a tumor.

3. The method of claim 1, wherein the second structure includes an organ at risk.

4. The method of claim 1, wherein adjustment of the treatment plan is based upon the planned dose that would be delivered to the patient during the one treatment fraction.

5. The method of claim 4, wherein adjustment of the treatment plan is based upon a comparison of an adjusted fraction dose to the planned dose to be delivered.

6. The method of claim 5, further comprising using a computer to incorporate the cumulative dose delivered to date.

7. The method of claim 5, further comprising using a computer to incorporate planned doses for subsequent fractions.

8. The method of claim 1, wherein identification of the position of a first structure relative to a second structure includes using internal landmarks.

9. The method of claim 8, wherein the internal landmarks includes fiducial markers.

10. The method of claim 1, wherein identification of the position of a first structure relative to a second structure includes using surrogates.

11. The method of claim 1, wherein identification of the position of a first structure relative to a second structure includes using an image acquisition device to acquire an image of the patient.

12. The method of claim 11, further comprising using a computer to analyze the acquired image to obtain biological or anatomical information about the patient.

13. The method of claim 1, wherein using a computer to prepare the treatment plan having multiple treatment fractions includes using a computer to calculate a total planned delivered dose to the patient.

14. The method of claim 13, wherein using a computer to calculate the total planned delivered dose includes using a computer to calculate a total planned dose to be delivered to a tumor volume and a total planned dose to be delivered to a non-tumorous structure that is located in physical proximity to the tumor volume.

15. The method of claim 14, wherein increasing or decreasing the dose to be delivered during the treatment fraction based upon the acquired information reduces the total planned dose to be delivered to the non-tumorous structure while allowing the total planned dose to be delivered to the tumor volume.

16. The method of claim 1, wherein using a computer to prepare the treatment plan includes using a computer to calculate a total biological effect to the patient, and wherein the total biological effect includes tumor control probability.

17. A method of treating a patient with radiation therapy using a plurality of fractions to deliver a total planned radiation dose to a tumor volume that has a sensitive structure in physical proximity to a tumor volume, the method comprising:
using a computer to prepare a treatment plan for a patient, the treatment plan including multiple treatment fractions each having a planned delivered dose;
after the treatment plan is prepared, acquiring an image of the patient with an image acquisition device;
using a computer to adjust the dose to be delivered for a given treatment fraction based on a position of the tumor volume relative to a sensitive structure shown in the acquired image; and
delivering radiation, with a radiation delivery device, to the patient according to the treatment plan such that the adjusted dose is delivered to the patient.

18. The method of claim 17, wherein information about the patient is obtained from the acquired image and includes at least one of tumor volume size, tumor volume position, and sensitive structure position.

19. The method of claim 17, wherein using the acquired image to adjust the dose to be delivered for a given fraction includes increasing the planned delivered dose for the fraction.

20. The method of claim 17, wherein using the acquired image to adjust the dose to be delivered for a given fraction includes decreasing the planned delivered dose for the fraction.

21. The method of claim 17, wherein using a computer to adjust the dose to be delivered for a fraction reduces the total planned radiation dose delivered to the sensitive structure while maintaining the total planned radiation dose delivered to the tumor volume.

22. The method of claim 17, wherein using a computer to adjust the dose to be delivered for a given fraction reduces the total number of fractions delivered to the patient while maintaining the total planned radiation dose delivered to the tumor volume.

23. The method of claim 17, wherein using a computer to adjust the dose to be delivered for a fraction reduces the total biological effect to the sensitive structure while maintaining the same anticipated biological effect to the tumor volume.

24. The method of claim 17, wherein using a computer to adjust the dose to be delivered for a given fraction includes an optimization procedure.

25. The method of claim 24, wherein using a computer to adjust the dose to be delivered using the optimization procedure incorporates the cumulative dose delivered and the biological effect to the patient to date.

26. The method of claim 24, wherein using a computer to adjust the dose to be delivered using the optimization procedure incorporates the expected future dose to be delivered and the biological effect to the patient.

27. The method of claim 17, wherein using a computer to adjust the dose to be delivered for a given treatment fraction based on the acquired image is done without doing a dose calculation.

28. The method of claim 17, wherein using a computer to adjust the dose to be delivered for a given treatment fraction based on the acquired image includes using an on-line dose calculation to evaluate how much to adjust the dose to be delivered for that given fraction.

29. The method of claim 17, wherein using a computer to adjust the dose to be delivered for a given treatment fraction based on the acquired image includes utilizing the cumulative dose delivered to date.

30. The method of claim 17, wherein using a computer to adjust the dose to be delivered for a given treatment fraction based on the acquired image uses an extrapolation of what the patient's anatomy is expected to do on subsequent days for subsequent treatment fractions.

31. The method of claim 17, wherein using a computer to adjust the dose to be delivered for a given treatment fraction based on the acquired image incorporates a biological model for dose accumulation and the effect of varying fraction sizes on the outcomes to the patient.

32. The method of claim 17, wherein using a computer to adjust the dose to be delivered for a given treatment fraction based on the acquired image includes using deformation.

33. The method of claim 17, wherein using a computer to adjust the dose to be delivered for a given treatment fraction based on the acquired image is done in tandem with another adaptive strategy.

34. The method of claim 33, wherein the other adaptive strategy includes one of altering the plan and selecting an appropriate plan from a previously prepared library of plans.

35. The method of claim 17, wherein using a computer to adjust the dose to be delivered for a given treatment fraction based on the acquired image incorporates qualitative or quantitative assessments of the biological effect on the patient.

36. The method of claim 35, wherein the biological effect on the patient includes at least one of tumor regression, patient tolerance, and patient side effects.

37. A radiation therapy treatment system for adapting a treatment plan, the radiation therapy treatment system comprising:
- a radiation delivery device; and
- a computer processor operatively coupled to the radiation delivery device, the computer processor having
  - a computer readable medium including instructions that cause the computer processor to
  - generate a treatment plan for a patient, the treatment plan including multiple treatment fractions each having an associated planned delivered dose to be delivered to the patient,
  - identify a first position of a first structure relative to a second structure prior to delivery of each one of the fractions, the identification being performed after the treatment plan is prepared,
  - prior to delivery of the present treatment fraction, identify a second position of the first structure relative to the second structure,
  - adjust the planned radiation dose to be delivered to the patient for the present treatment fraction based on the second position of the first structure relative to the second structure without the treatment plan being replanned, and
  - instruct the radiation delivery device to deliver the adjusted planned radiation dose to the patient.

38. A computer program stored on a non-transitory machine-readable medium capable of being executed by a computer, the computer program for use in a radiation therapy treatment system, the computer program comprising:
- a treatment plan module operable to generate a treatment plan for a patient, the treatment plan including multiple treatment fractions each having an associated planned delivered dose to be delivered to the patient;
- a patient position module operable to identify a first position of a first structure relative to a second structure prior to delivery of each one of the fractions, the identification being performed after the treatment plan is prepared;
- a fraction modification module operable to, prior to delivery of the present treatment fraction, identify a second position of the first structure relative to the second structure and adjust the planned radiation dose to be delivered to the patient for the present treatment fraction based on the second position of the first structure relative to the second structure without the treatment plan being replanned; and
- a treatment delivery module operable to instruct a radiation delivery device to deliver the adjusted planned radiation dose to the patient.

39. The method of claim 1, wherein adjustment of the planned radiation dose to be delivered to the patient includes increasing the dose to be delivered for the present treatment fraction based on the second position of the first structure relative to the second structure.

* * * * *